US008683435B2

(12) United States Patent
Richards et al.

(10) Patent No.: US 8,683,435 B2
(45) Date of Patent: Mar. 25, 2014

(54) SYSTEM AND METHOD FOR CONFIGURING ELECTRONIC DATA CAPTURE AND DATA MANAGEMENT SYSTEMS FOR CLINICAL TRIALS

(75) Inventors: Nicholas P. Richards, Mission Viejo, CA (US); James A. Langford, Dove Canyon, CA (US); Richard E. Gleeson, Warrington, PA (US); Scott Thompson, Orange, CA (US); Christopher C. DeMeyer, Lee Summit, MO (US); Ron W. Dixon, Santa Ana, CA (US); Dennis M. Wjinker, Laguna Niguel, CA (US); Robert L. Barr, Aliso Viejo, CA (US)

(73) Assignee: Datalabs, Irvine, CA (US)

( * ) Notice: Subject to any disclaimer, the term of this patent is extended or adjusted under 35 U.S.C. 154(b) by 1700 days.

(21) Appl. No.: 11/045,789

(22) Filed: Jan. 28, 2005

(65) Prior Publication Data

US 2006/0174210 A1    Aug. 3, 2006

(51) Int. Cl.
| | |
|---|---|
| *G06F 9/44* | (2006.01) |
| *G06Q 10/00* | (2012.01) |
| *G06Q 50/00* | (2012.01) |
| *G06F 17/00* | (2006.01) |
| *G06F 17/20* | (2006.01) |
| *G06F 17/21* | (2006.01) |
| *G06F 17/22* | (2006.01) |
| *G06F 17/24* | (2006.01) |
| *G06F 17/25* | (2006.01) |
| *G06F 17/26* | (2006.01) |
| *G06F 17/27* | (2006.01) |
| *G06F 17/28* | (2006.01) |

(52) U.S. Cl.
USPC ........... 717/121; 717/104; 717/105; 717/106; 717/109; 717/120; 705/2; 705/3; 715/221; 715/222; 715/223

(58) Field of Classification Search
None
See application file for complete search history.

(56) References Cited

U.S. PATENT DOCUMENTS 7,376,670 B2 * 5/2008 Badt et al. .............................. 1/1
2004/0249664 A1 * 12/2004 Broverman et al. .............. 705/2

FOREIGN PATENT DOCUMENTS

WO    WO 02/101496 A    12/2002

OTHER PUBLICATIONS

Brochure: "Datalabs XC™ Accelerating Clinical Development," DataLabs, to the best of the undersigned's information and belief Summer 2004.
Brochure: "You can't do it without three." DataLabs Worldwide, to the best of the undersigned's information and belief Summer 2002.
Brochure: "At some point, they'll need to talk. So will you clinical development systems." DataLabs Worldwide, to the best of the undersigned's information and belief Summer 2002.

(Continued)

*Primary Examiner* — Lewis A Bullock, Jr.
*Assistant Examiner* — Mark Gooray
(74) *Attorney, Agent, or Firm* — Wolf, Greenfield & Sacks, P.C.

(57) ABSTRACT

The present invention includes aspects of a designer program or tool for customizing a clinical trial program to a particular protocol of a particular clinical trial. The designer program includes visual cues or mechanisms for organizing trial components within the designer program in a straightforward manner such that technically low skilled designers can implement often complex trial protocols. In an embodiment, the designer program includes validation scripts that test functions, derivations, queries and the like. Moreover, use of the designer program can include development of trial libraries that can make customizations reusable, scalable, and highly efficient.

24 Claims, 51 Drawing Sheets

(56) References Cited

OTHER PUBLICATIONS

"Datalabs XC © Accelerating Clinical Development" DATALABS, Online, Mar. 30, 2004, XP002351325, Retrieved from the Internet: URL:http://datalabs.com/DatalabsTrifoldPDF.pdf> retrived on Oct. 26, 2005, p. 3.

Egar, John W., M.D. et al., "Diagrammatic Acquisition of Medical Information for Clinical Trials," Medinfo 92. Proceedings of the Seventh World Congress on Medical Informatics Sep. 6-10, 1992, Geneva, Switzerland, 1992, pp. 1330-1336, vol. XP002351326, Medinfor 92. Proceedings of the Seventh World Congress on Medical Informatics North-Holland Amsterdam Netherlands ISBN: 0-444-89668-6 abstract; figure 1, p. 1332, line 35, p. 1332, last line, p. 1333, line 6-line 14.

Duftschmid, Georg et al., "Management of data from clinical trails using the ArchMed System," Medizinische Uniersitat Wien, Online, Jun. 2002, pp. 1-24, XP002351327, Retrieved from the Internet: URL:http://ww.meduniwien.ac.at/msi/mias/papers/Duftschmid2002b.pdf> retrieved on Oct. 26, 2005, p. 15, paragraph 2-paragraph 3, p. 8, line 4-p. 10, line 9, p. 5, paragraph 3 abstract & Medical Informatics and the Internet in Medicine Taylor & Francis UK, vol. 27, No. 2, Jun. 2002, pp. 85-98, ISSN: 1463-9238.

Gall, W. et al., "A Clinical Form Designer," Medizinische Universitat Wein, Online, Jun. 25, 2001, pp. 1-4, XP002351328, Retrieved from the Internet: URL:http://www.meduniwein.ac.at/msi/mias/papers/Gall2001a.pdf> retrieved on Oct. 26, 2005, p. 2, right-hand column, paragraph 2.3; figure 1 & W.Gall et al: "A Clinical from Designer," Proceedings of the 2001 International Conference of Mathematics and Engineering Techniques in Medicine and Biological Sciences (METMBS'2001), 2001, Las Vegas, Nevada, USA (CSREA Press).

Jay, Julien, "ActiveWin: Microsoft Visio 2000 Professional—Review" Activenetwork, Online, Oct. 27, 2005, XP002351329, retrieved from the Internet: URL:http://www.activewin.com/reviews/software/apps/ms/visio2k/index.shtml>, retrieved on Oct. 26, 2005 the whole document.

PCT International Search Report, App. No. PCT/US 2005/003426, App. Date: Nov. 9, 2005, 5 pages.

* cited by examiner

200

| Shape (202) | Represents or Defines (204) |
|---|---|
| *Study* | Study name, study description, protocol number, protocol description, or the like |
| Form | Form name, form display name, whether it can be used within an unscheduled event, or the like |
| Event | Event name, event order, associated forms, or the like |
| | Event minimum, ideal, or maximum event windows may be defined based on previous event dates or visits |
| Common Event | Event display name, display order (i.e. first or last), associated forms, or the like |
| Patient State | Different patient statuses that a patient can obtain, patient state display name, associated icon, action display name column header display name, or the like |
| Patient State Transition | Connects the Patient State shapes in a manner that defines what patient state a patient can transition to from a previous state. |
| Path | Unique patient pathway (i.e. sequence of patient events) |
| Group | A listing of data items, group name, group domain reference, name, data type, code list reference, min/max length, min/max precision, derivation reference, derivation reference, dictionary reference, comments, or the like |
| Domain | Logical categories that are used to organize groups for the purpose of reporting and for data exports, name of the domain, or the like |
| CodeList | Value pairs, a display value, a stored value, a default value pair, code list name, or the like |
| Dictionary | Encoding dictionaries, dictionary name, type, version, or the like |
| Question | Fields displayed on forms, question name, display order, question display prompt, data item reference, conditional logic, or the like |
| Table | Table of questions, columns of data to be captured, table name, display order, table display prompt, or the like |
| Info Question | Text, graphics, optional tags, such as HTML tags, or the like |
| Derivation | Logic, derivation name, description, parameter references, script, test values, or the like |

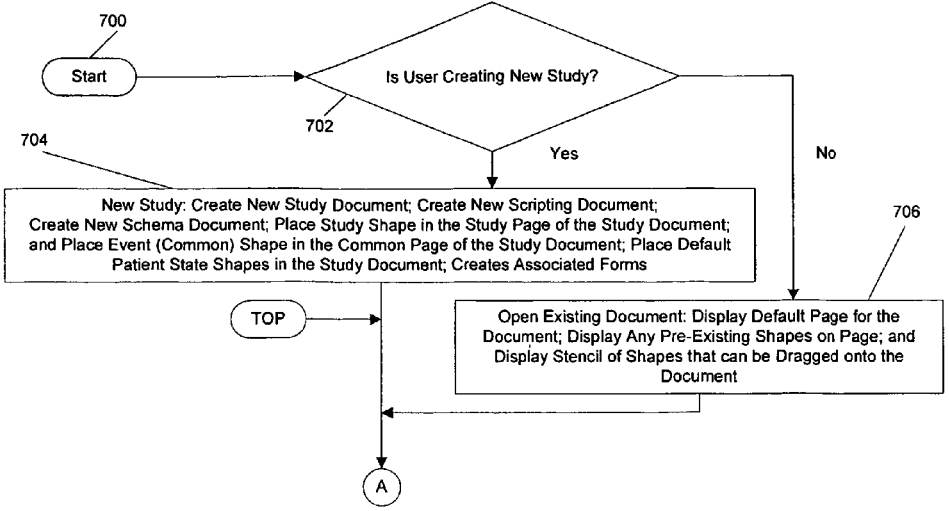
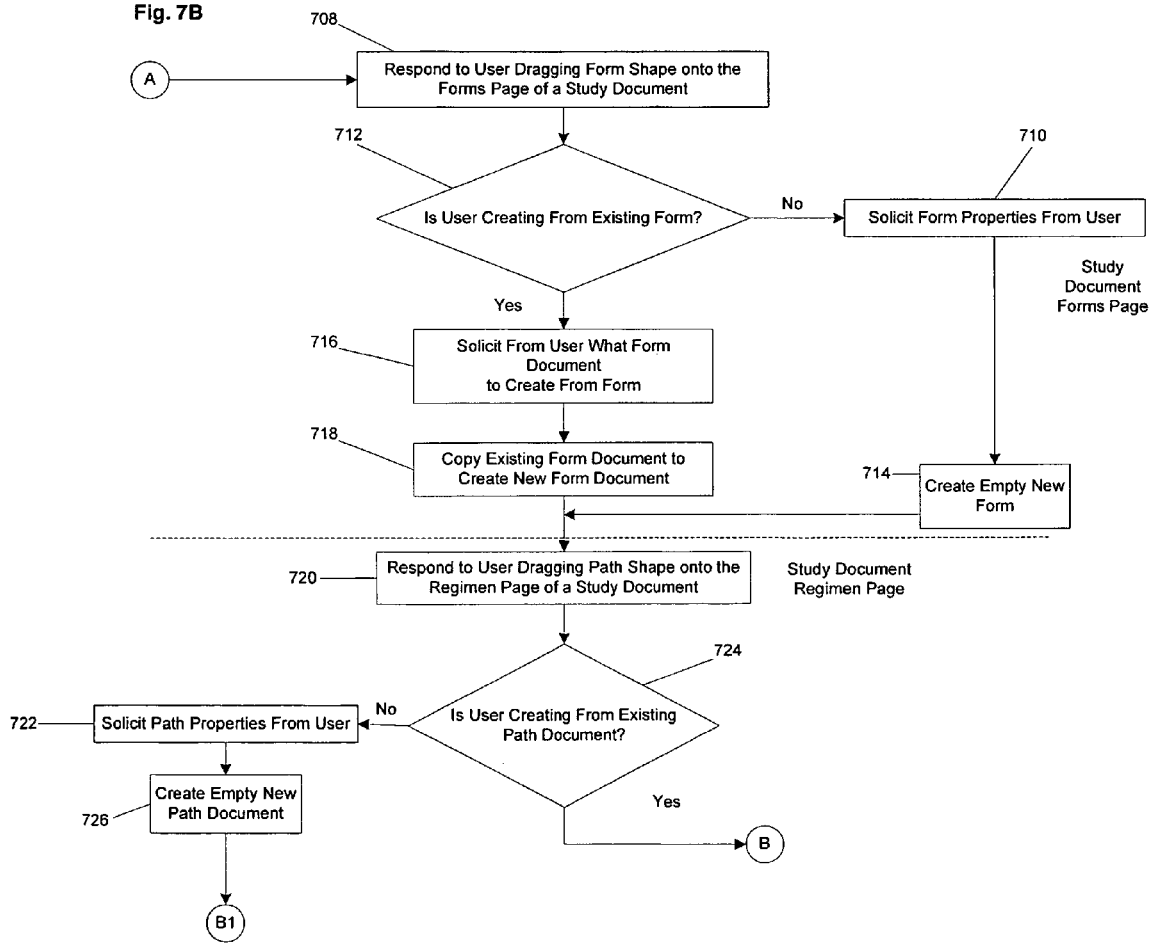

FIG. 8D

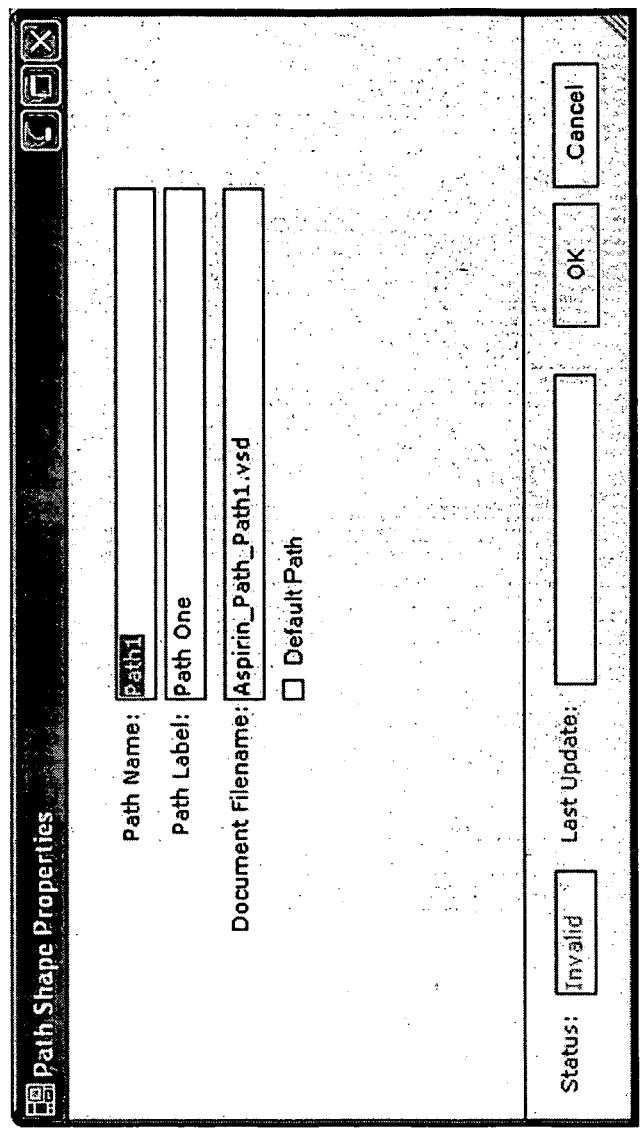

FIG. 8F

Event Shape Properties

- Event Name: Visit01
- Event Label: Screening
- Event Type: Scheduled
- Event Order: 1
- Publish Event on: Screened
- External Event ID:
- CDISC Event Category:

Forms [Window]

☐ Use Event Schedule Window

- Window Reference Event:
- Window Minimum: 0
- Window Ideal: 0
- Window Maximum: 0
- Unit of Time: Days Status: Valid    Last Update: 12/8/2004 4:04:24 PM OK    Cancel 8F-1

Group Properties

Group Name: ConMed
Group Label: Concomitant Medications
Domain: ConMed

| Item Name | DataType | Code List | MinPre | MaxPre | MinLen | MaxLen | Dictionary | Derivation | Domain | Comments |
|---|---|---|---|---|---|---|---|---|---|---|
| Indication | Text | | | | 0 | 100 | Drugs | | | |
| Medication | Text | | | | 0 | 100 | Drugs | | | |
| StartDate | Date | | | | 10 | 10 | | <Unassigned> | | |
| EndDate | Date | | | | 10 | 10 | | | | |
| PossInteractions | Text | | | | 0 | 100 | Conditions | | | |

Add New    Delete

Status: Valid    Last Update: 12/8/2004 4:04:28 PM    OK    Cancel

FIG. 8H

Code List Properties

Code List Name: TimeUOM
Code List Label: Time Unit of Measure
CDISC: SAS Format Name:

| Code Label | Code Value |
|---|---|
| [Blank] | 0 |
| seconds | SEC |
| minutes | MIN |
| hours | HR |
| days | DAY |
| weeks | WK |
| months | MON |
| years | YR |

Add New   Delete

Status: Valid   Last Update: 12/8/2004 4:04:29 PM

OK   Cancel

SYSTEM AND METHOD FOR CONFIGURING ELECTRONIC DATA CAPTURE AND DATA MANAGEMENT SYSTEMS FOR CLINICAL TRIALS

BACKGROUND OF THE INVENTION

1. Field of the Invention

The present invention generally relates to clinical trials. In particular, the present invention relates to configuring a clinical trial program to implement a particular protocol of a particular clinical trial.

2. Description of the Related Art

Before a new medical drug (e.g., pharmaceuticals) or device (e.g., surgical instruments or implants) may be dispensed to the public, the United States Food and Drug Administration (FDA) requires that the manufacturers of the pharmaceuticals, devices, instruments, or implants conduct extensive clinical trial research in order to demonstrate the clinical effectiveness, safety, and medical advantage of their products. Extensive and often complex clinical trial protocols are developed that define, for example, targeted demographics, proposed medications, patient regimens, forms for collection, types of statistically relevant data, the timing or order of events within the study, often even the layout of the reporting data, and the like. These protocols are often sufficiently complex that the protocols themselves receive FDA approval.

Once a protocol is developed and approved, companies design electronic data capture and data management solutions to manage the ever burgeoning amount of data gathered. In general, such data capture and data management solutions capture data from geographically disparate clinicians or study participants defining many points of data entry, potentially across many software and hardware platforms. Drawbacks of these systems include the costs associated with designing, customizing, and/or adapting particular proprietary data capture and data management systems to the ever changing needs presented with each new protocol of each new clinical trial. Thus, many of today's sponsors resort to highly-skilled technology personnel, such as computer programmers or system designers, to adapt their systems, particularly their database and data storage systems, to each protocol. Use of such personnel can be time-consuming, costly, difficult to replicate over somewhat trivial changes, and can lack scalability.

As one may suppose, manufacturers of the pharmaceuticals, devices, instruments, or implants invest millions of dollars conducting the foregoing clinical trials before they receive any revenue from a sale of their products. For example, a rough estimate may be as long as 12 to 15 years to bring a drug to market at a cost of over $800 million. Accordingly, sponsors are eager to lower the cost and complexity associated with clinical trials.

SUMMARY OF THE INVENTION

As will be described in greater detail below, the present invention seeks to overcome one or more of the foregoing drawbacks and potentially significantly lower costs by providing a designer program that can rapidly design, prototype, test, implement and deploy electronic data capture and data management systems configured for new or altered protocols for new or altered clinical trials. Various embodiments of the designer program include straightforward visual cues or mechanisms, such as shapes, which allow designers to configure data capture and data management software systems through straightforward actions such as drag and drop, double click, or the like. Moreover, various embodiments of the designer program may provide for library functionality allowing for advanced scalability and reproducibility throughout the design process. Also, embodiments of the designer program provide trial validation through, for example, positive and negative testing of scripting programs or error correction. Moreover, the designer program may advantageously acquire protocol documents, such as, for example, structured documents, flowcharts, or the like, and, in some cases, automatically or substantially automatically generate some or all of the configuration data usable to configure data capture and data management software systems.

For example, an embodiment of the present disclosure includes a designer program for straightforward configuring of a data capture and data management system, such as a web based study engine that allows for geographically disparate points of data entry, collection, and management, across differing hardware and software systems. The study engine and its backend database systems may advantageously incorporate one or more configuration files that govern, or otherwise configure the study engine and database systems for a given protocol of a given clinical trial. Such study engines are commercially available from, for example, DataLabs Corporation of Irvine, Calif., under the name of "DataLabsXC Clinical."

Use of a designer program or tool for customizing electronic data capture and data management systems, such as DataLabsXC Clinical, to a particular clinical trial advantageously reduces costs and complexity by standardizing the configuration of such systems to the point where relatively low technically skilled designers are capable of implementing any desired customizations.

For purposes of summarizing the invention, certain aspects, advantages, and novel features of the invention have been described herein. Of course, it is to be understood that not necessarily all such aspects, advantages or features will be embodied in any particular embodiment of the invention.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIGS. 7A through 7G combined form a flow chart illustrating another embodiment of a process for designing a clinical trial using an embodiment of the designer program of FIG. 1.

FIGS. 8A through 8P-3 are exemplary simplified screen views illustrating embodiments and properties for each shape of the designer program of FIG. 2.

DETAILED DESCRIPTION OF THE PREFERRED EMBODIMENT

In an effort to reduce the complexity of the present disclosure, the term "clinical trial program" will include its broad ordinary meaning to one skilled in the art as well as electronic data capture and data management systems that may provide for one or more of the entry, collection, storage, management, organization, analysis, error resolution, and reporting of data related to clinical trials.

Embodiments of the present disclosure include a straightforward designer program or tool for designing or adapting one or more configuration files usable by a clinical trial program to govern the specific collection and management needs of a clinical trial. In one embodiment, a designer program employs visual cues or mechanisms, such as shapes, that a designer can manipulate to create, reuse, or modify the configuration file. Selection of a visual mechanism prompts the designer for additional information through the display of a Properties screen. By selecting particular visual mechanisms, for example, shapes, and properly defining their associated properties, the designer tool essentially generates a visual "blueprint" or layout that will govern how the clinical trial program will interact with the users thereof to perform a protocol of a clinical trial. Specifically, the designer program can generate some or all of the configuration files from the visual layout, and upload the configuration file into the clinical trial program. The clinical trial program then accesses the configuration file to determine how to interact with clinicians, data entry personnel, other clinical trial participants or the like, to perform some or all of data capture, storage, error checking, testing, data analysis and reporting, workflow, or the like of a particular clinical trial. Thus, a technically low skilled designer can advantageously customize a clinical trial program to perform a defined protocol that may include capturing and managing data for potentially very complex, large, and diverse clinical trials across multiple software and hardware platforms.

In an embodiment, the designer program can include validation routines that allow for testing of various data validation or error checking scripts. The validation routines may include positive and negative testing scenarios adapted to advantageously test data validation at the time of design, rather than during implementation.

To facilitate a complete understanding of the invention, the remainder of the detailed description describes the invention with reference to the drawings, wherein like reference numbers are referenced with like numerals throughout.

Figure 1:
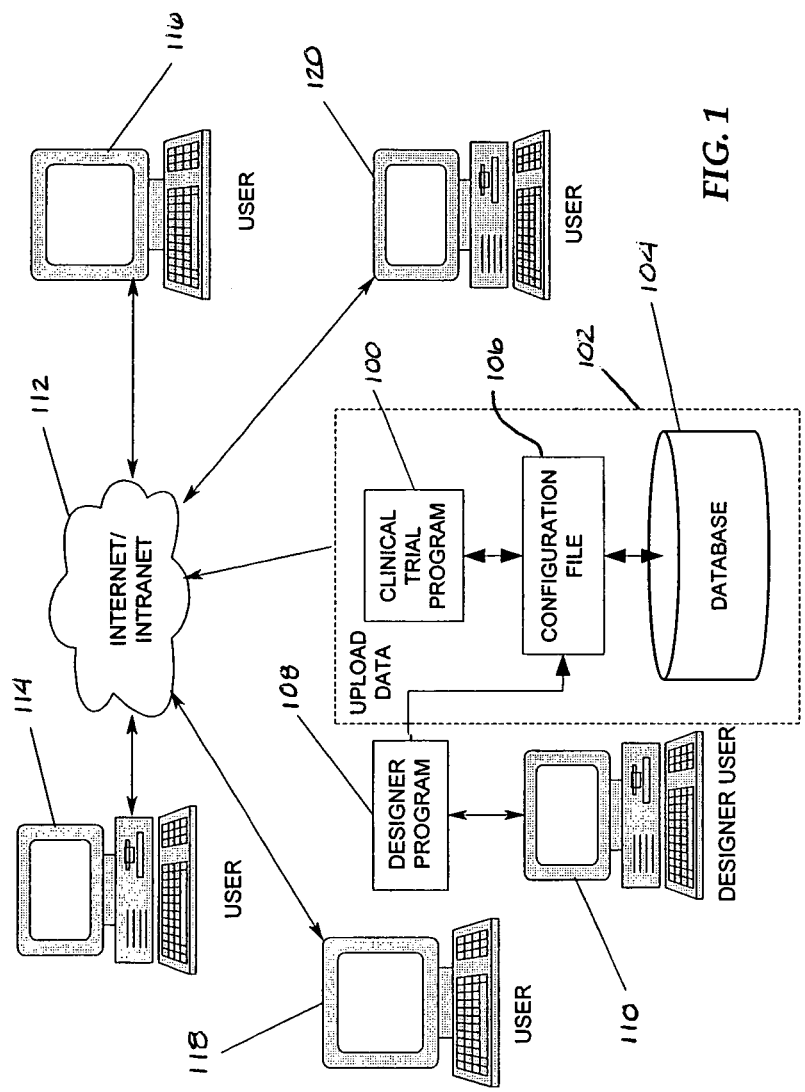
FIG. 1 is an exemplary generalized block diagram of a system for collecting and managing data as part of a clinical trial, including a clinical trial program configured through one or more configuration files and a designer program capable of generating the one or more configuration files, according to an embodiment of the invention.

Referring now to the drawings and to FIG. 1 in particular, a generalized block diagram illustrates a system for managing a clinical trial according to an embodiment of the invention. A clinical trial program 100 is executed by one or more computer systems 102. Program 100 has access to a database 104 for storing data received from trial participants. In an embodiment, the clinical trial program 100 provides, for example, a portal-based web collection tool that offers timely access to study data. In an embodiment, the clinical trial program 100 comprises a clinical trial program such as that commercially available from, for example, DataLabs Corporation of Irvine, Calif., under the name of "DataLabsXC Clinical."

In a preferred embodiment, the clinical trial program 100 includes software and hardware systems, including database systems 104, normalized to general clinical trial solutions. The clinical trial program 100 then advantageously accesses one or more configuration files 106 that the program 100 uses to customize its behavior to carry out a particular protocol for a particular clinical trial. By using configuration files 106, the clinical trial program 100 is advantageously highly customizable, scalable, and efficient.

According to a preferred embodiment, a designer program or tool 108 executes on one or more computer systems 110 to generate or modify the configuration files 106 through a straightforward user interface. The user interface may advantageously employ one or more audio or visual cues or mechanisms, such as shapes, that a user/designer can manipulate to create, reuse, modify, etc. the configuration files 106. Selection and customization of the visual mechanisms, such as shapes, provides an unskilled user/designer the tools for programming a protocol for the clinical trial program 100 such that the clinical trial program 100 executes a particular clinical trial. Details of the designer program 108 are amplified below; however, in a preferred embodiment, the designer program or tool 108 uses Microsoft Visio, or any other suitable shape-based software, for customizing the clinical trial 100 to a particular protocol.

In an embodiment, once the clinical trial program 100 receives the configuration files 106 designed on the designer program 108 by, for example, one or more technically low-skilled users, the clinical trial program 100 builds some or all the components that are used to conduct the clinical trial, which is now customized to a designated protocol. As used herein, the term "synchronizing" of a study includes its broad ordinary meaning known to one of ordinary skill in the art as well as including the process of the clinical trial program 100 building its components from instructions or data in the configuration file 106.

For purposes of an overall system description, the clinical trial program 100 can be linked to clinical trial participants through the Internet, an Intranet 112, combinations of the same, or the like. For example, participants or users 114, 116, 118, 120 ... may access the clinical trial program 100 through the Internet/Intranet 112. Users 114 through 120 interact with the clinical trial program 100, and data (along with the audit history and the like) generated from this interaction are stored in the database 104. For example, the clinical trial program 100 may advantageously provide the users 114 through 120 helpful prompts, real-time data correction and validation, and other feedback to successfully and accurately enter clinical data through a standard web browser.

As will be amplified further below, the user/designer designs the clinical trial by selecting various components or visual cues in the designer program 108 that provide the instructions for the clinical trial program 100 in order to build the clinical trial components. In an embodiment, some or all of these components are represented in an XML structure that can be uploaded to the clinical trial program 100 as one or more configuration files 106. At run-time, users 114 through 120 access the clinical trial program 100 and interact in varying capacities as part of the data entry and cleaning process. These interactions are recorded and compiled in the database 104 over a period of time for use by the pharmaceutical or device manufacturing company (or the FDA, or the like).

The term "XML" (i.e., Extensible Markup Language) will include its broad ordinary meaning known to one skilled in the art as well as including a computer language for documents comprising structured information, which usually includes both content (words, pictures, etc.) and some indication of what role that content plays (for example, content in a section heading has a different meaning from content in a footnote, which means something different than content in a figure caption or content in a database table, etc.).

Figure 3:
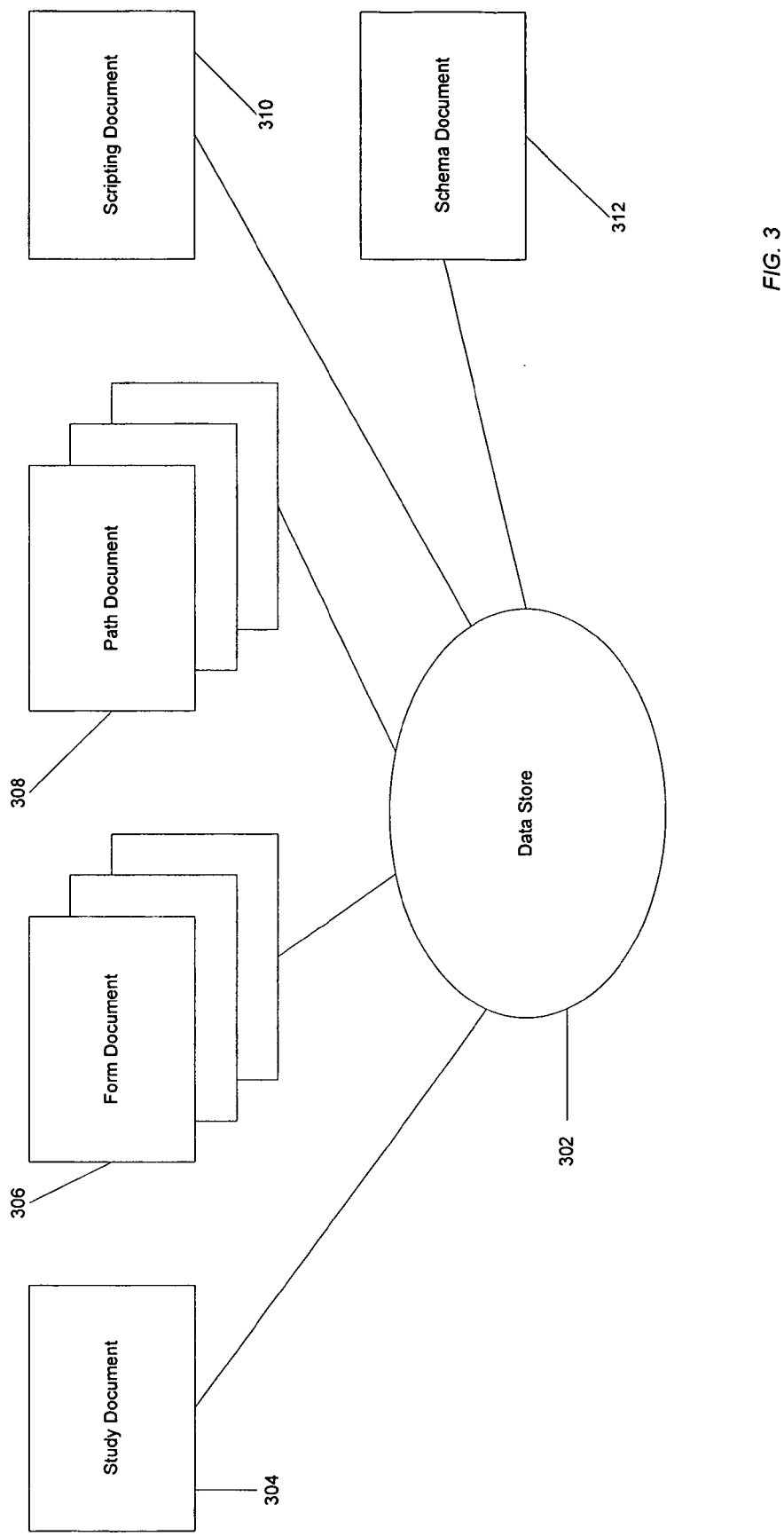
FIG. 3 is a block diagram illustrating documents and their interrelationships used by the designer program, according to an embodiment of the invention.
Figure 8A:
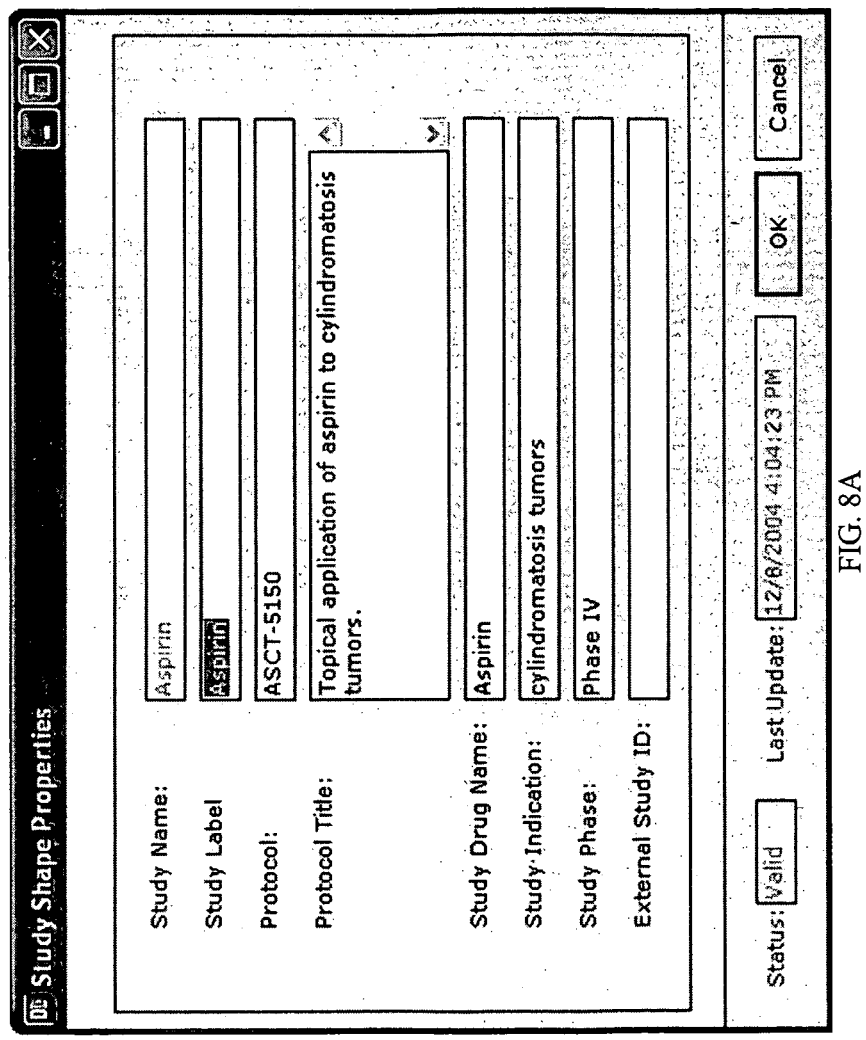
Figure 8B:
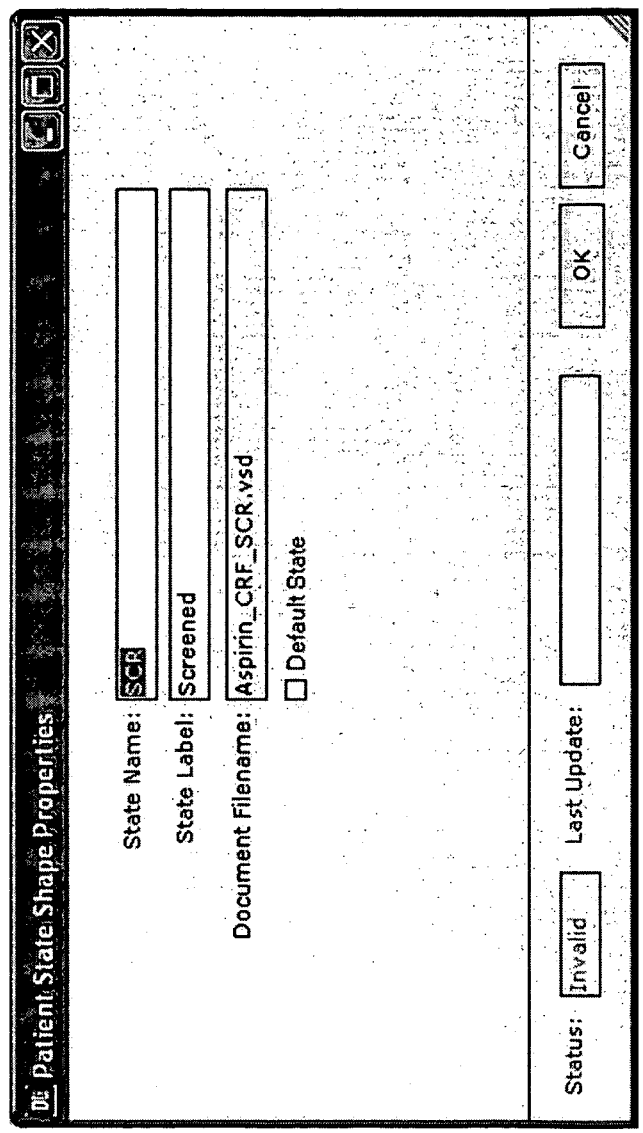
Figure 8C:
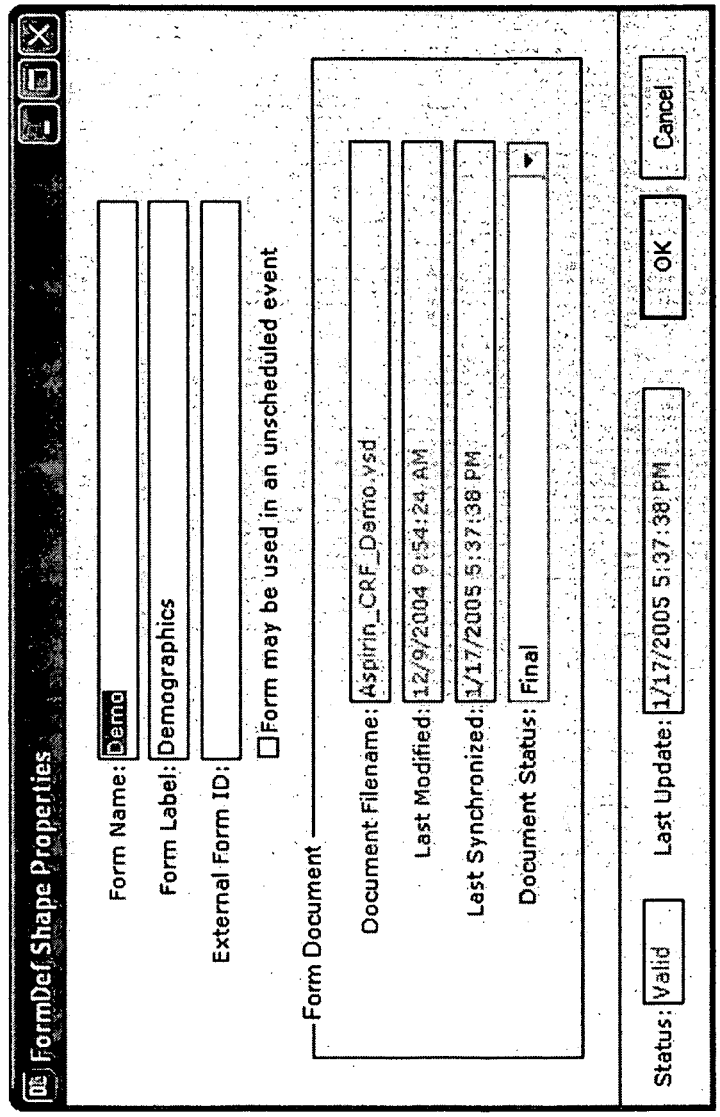
Figure 8D:
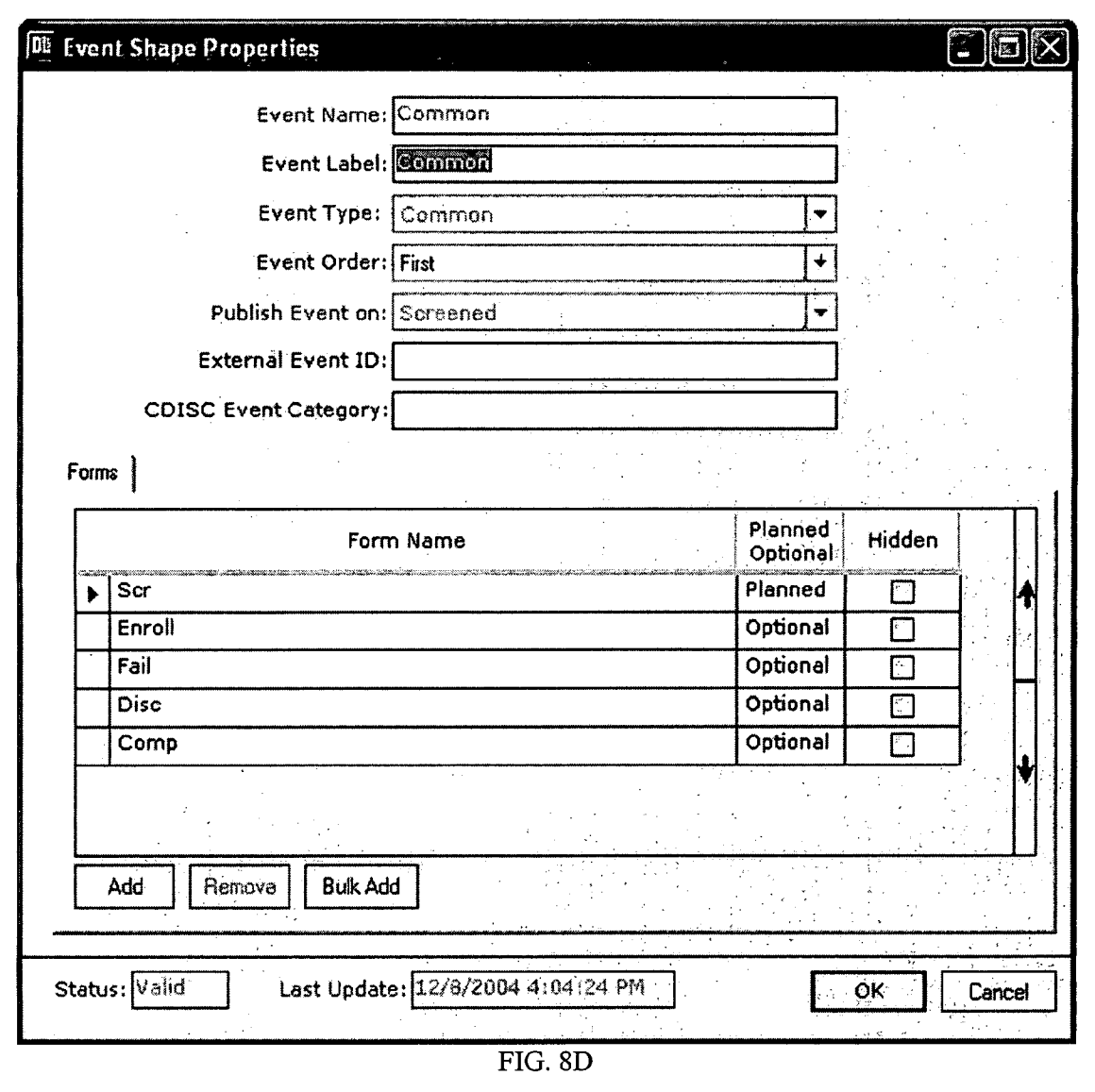
Figure 8F:
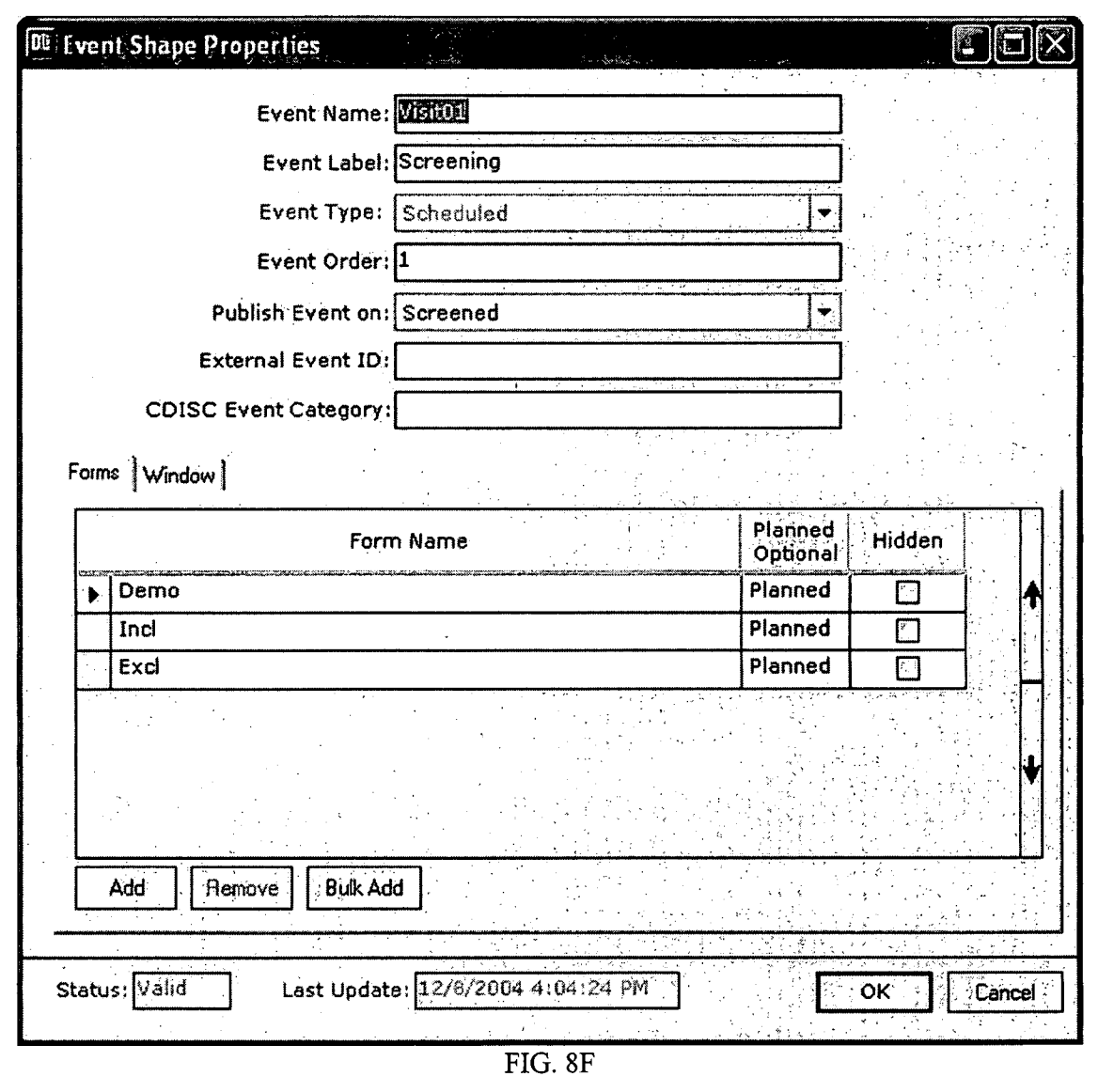
Figure 8G:
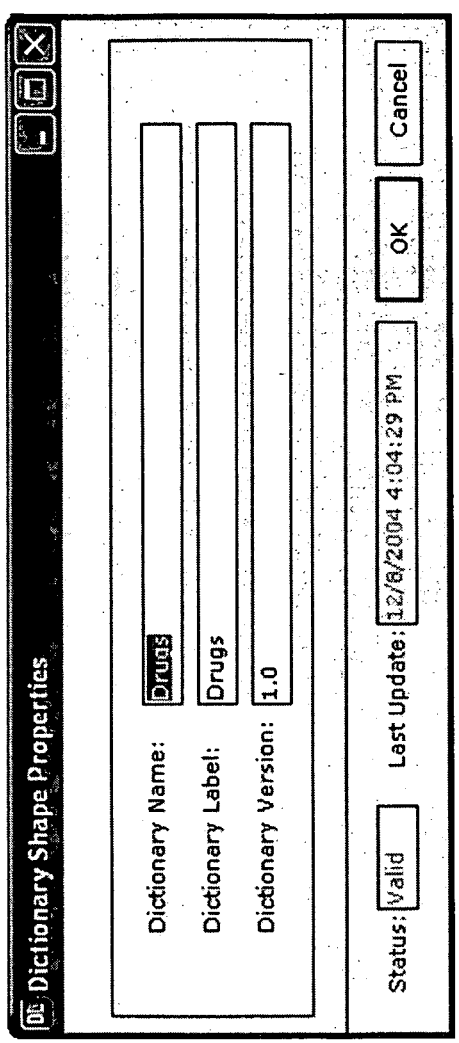
Figure 8I:
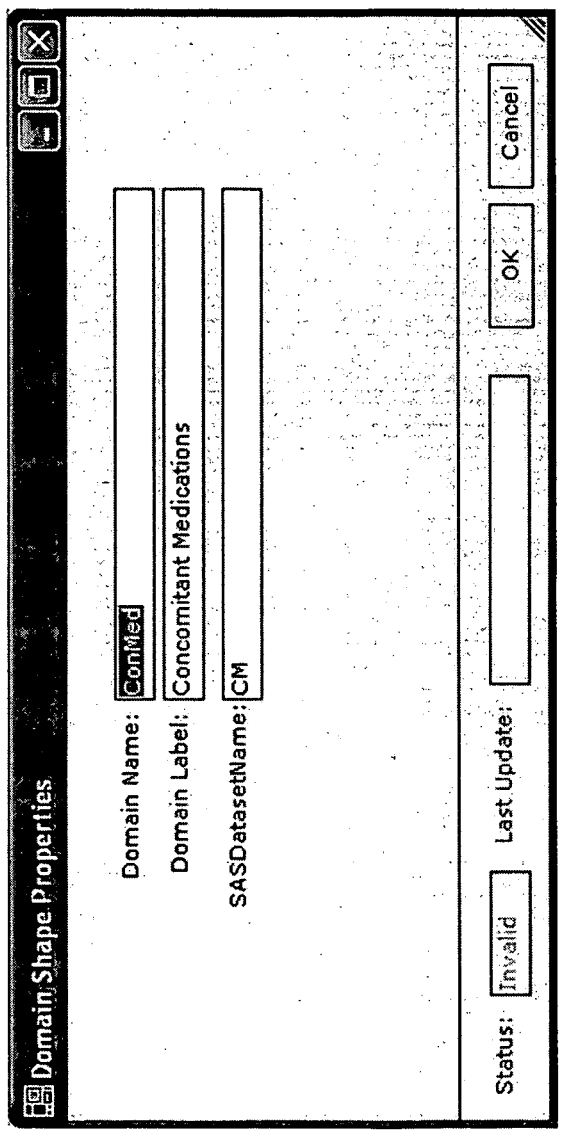
Figure 8K:
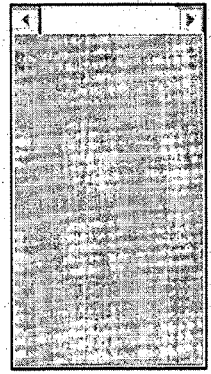
Figures 2, 8K:
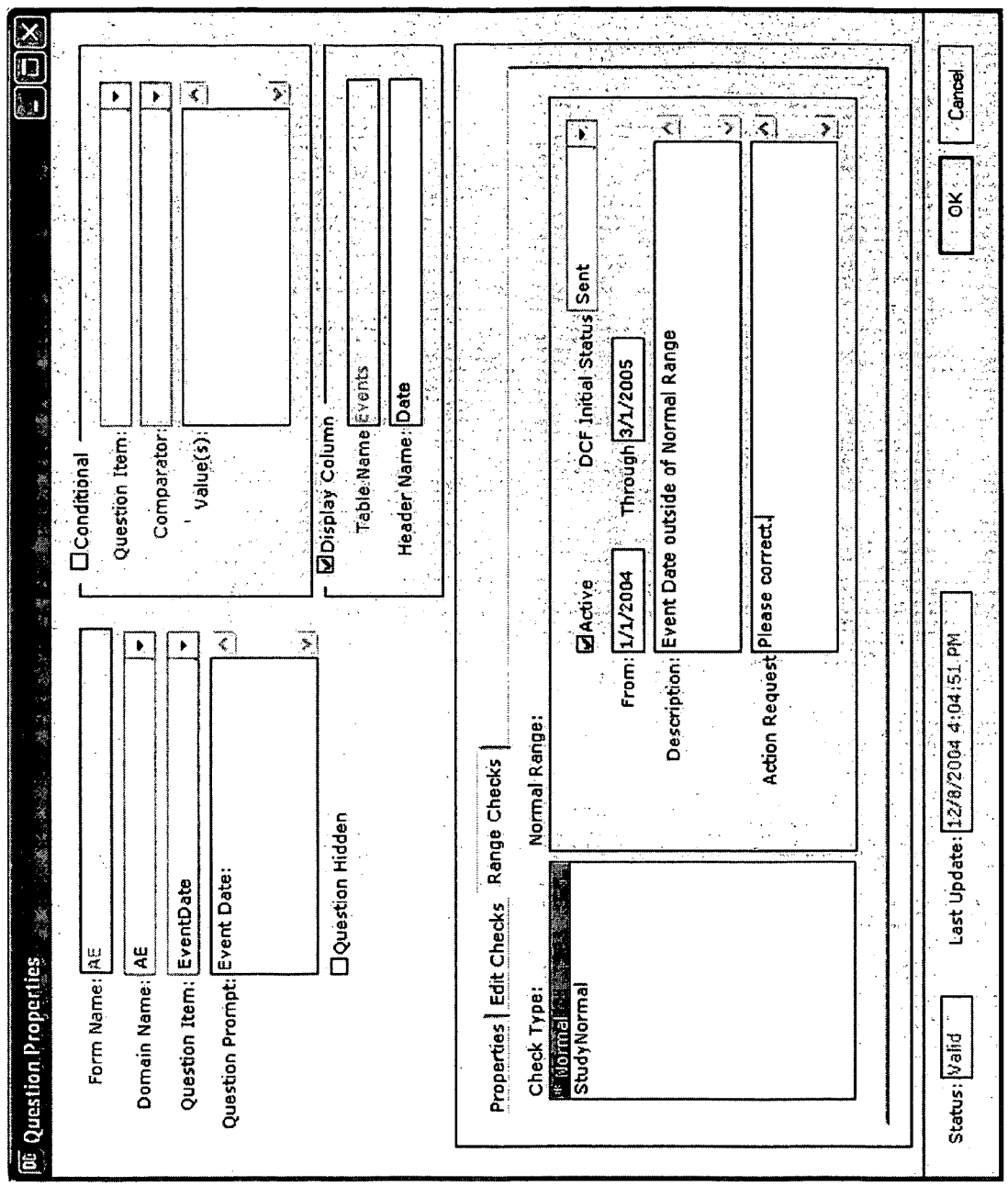
FIG. 2 is a table illustrating names and corresponding descriptions of exemplary visual cues or mechanisms of the designer program of FIG. 1.
Figure 8L:
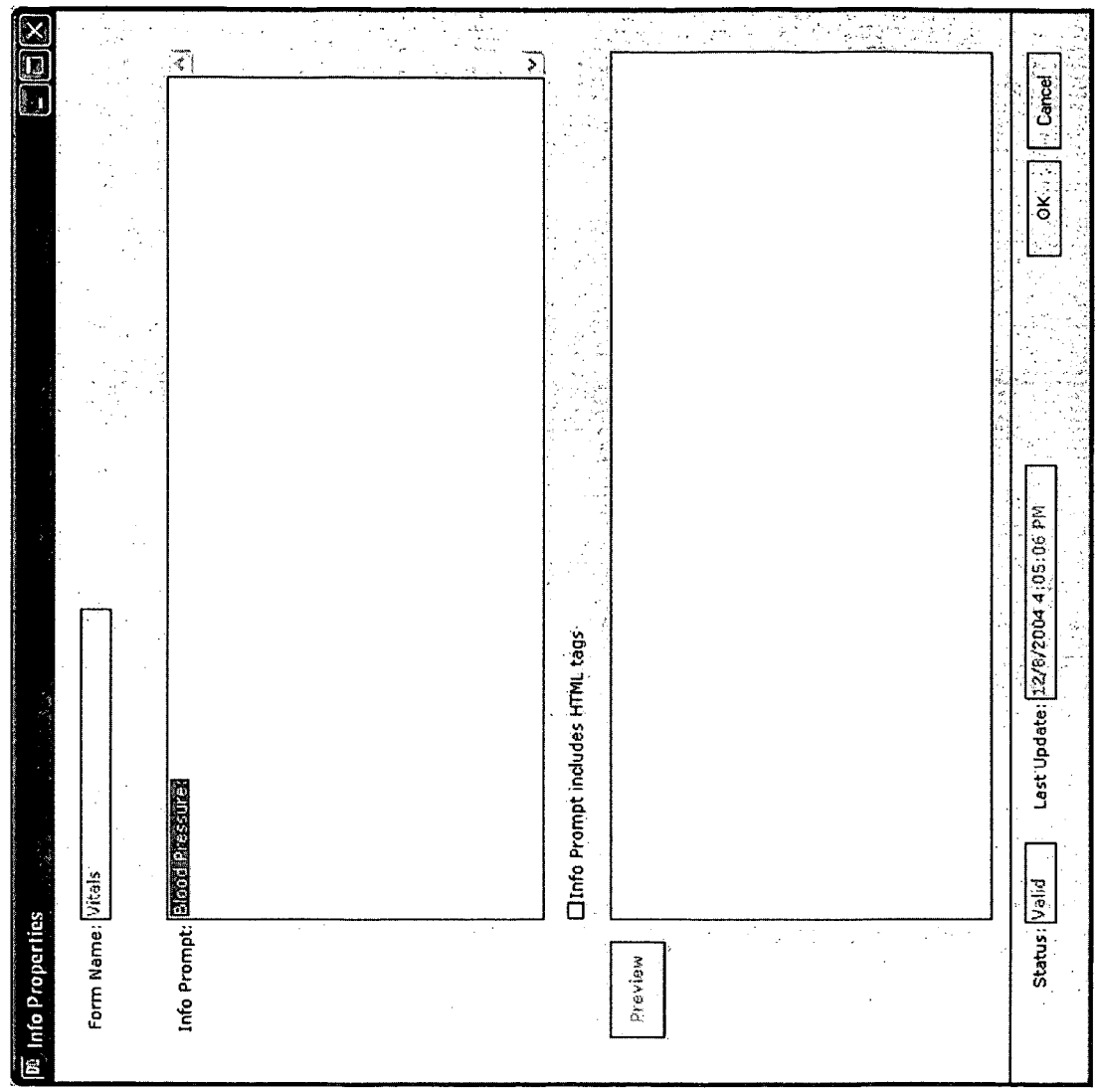
Figure 8M:
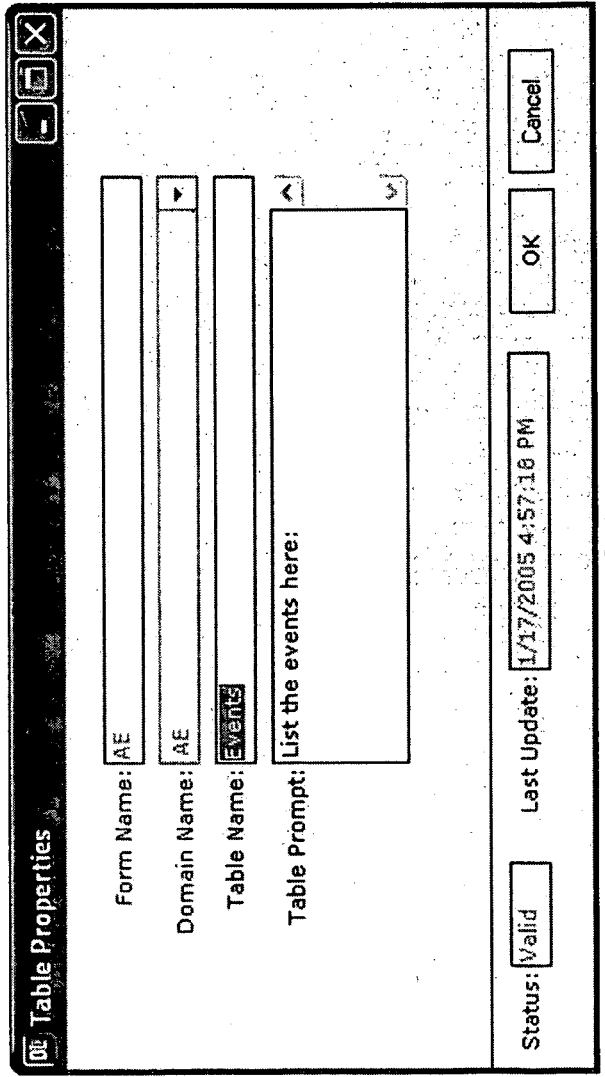
Figure 8N:
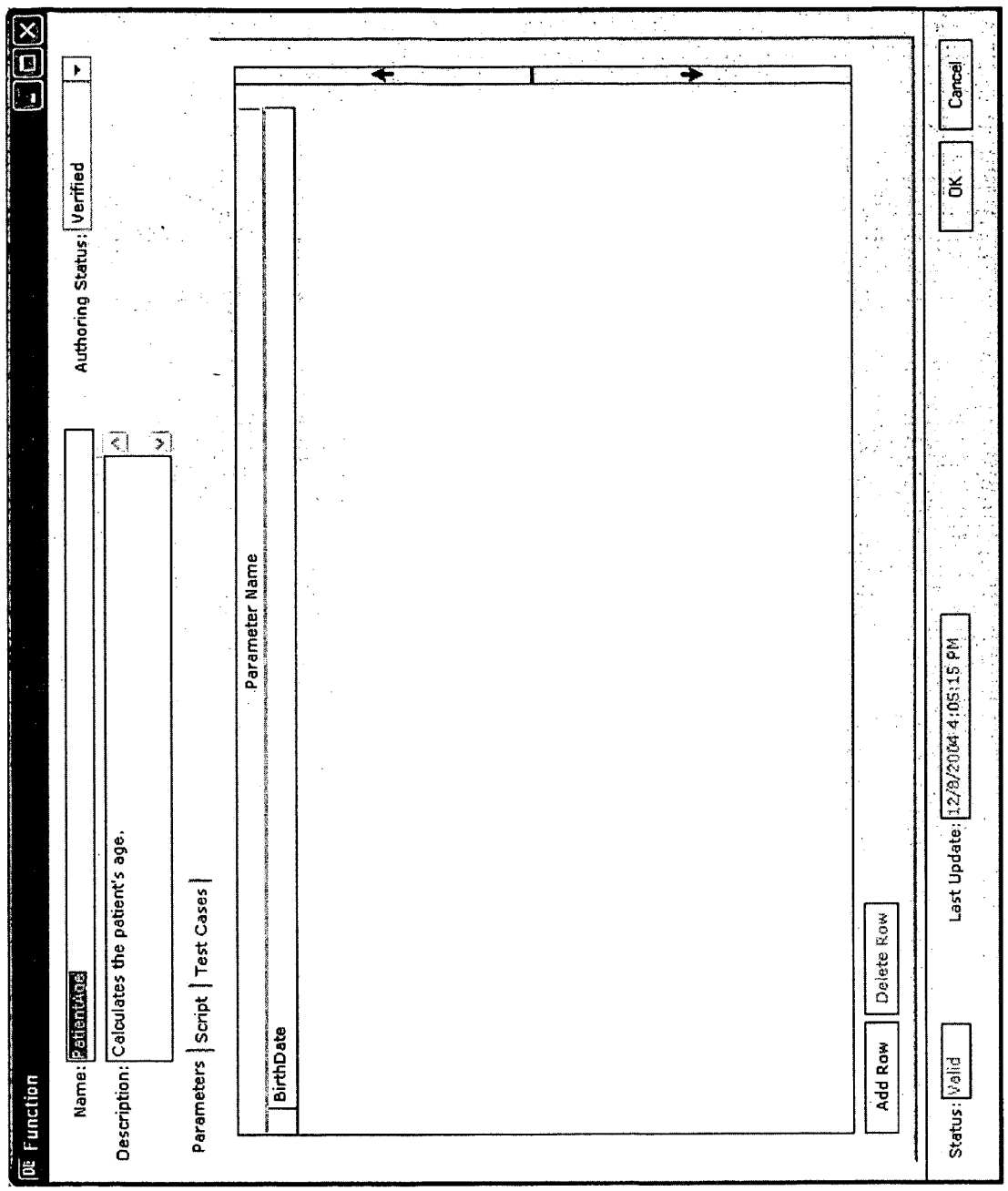
Figures 1, 8N:
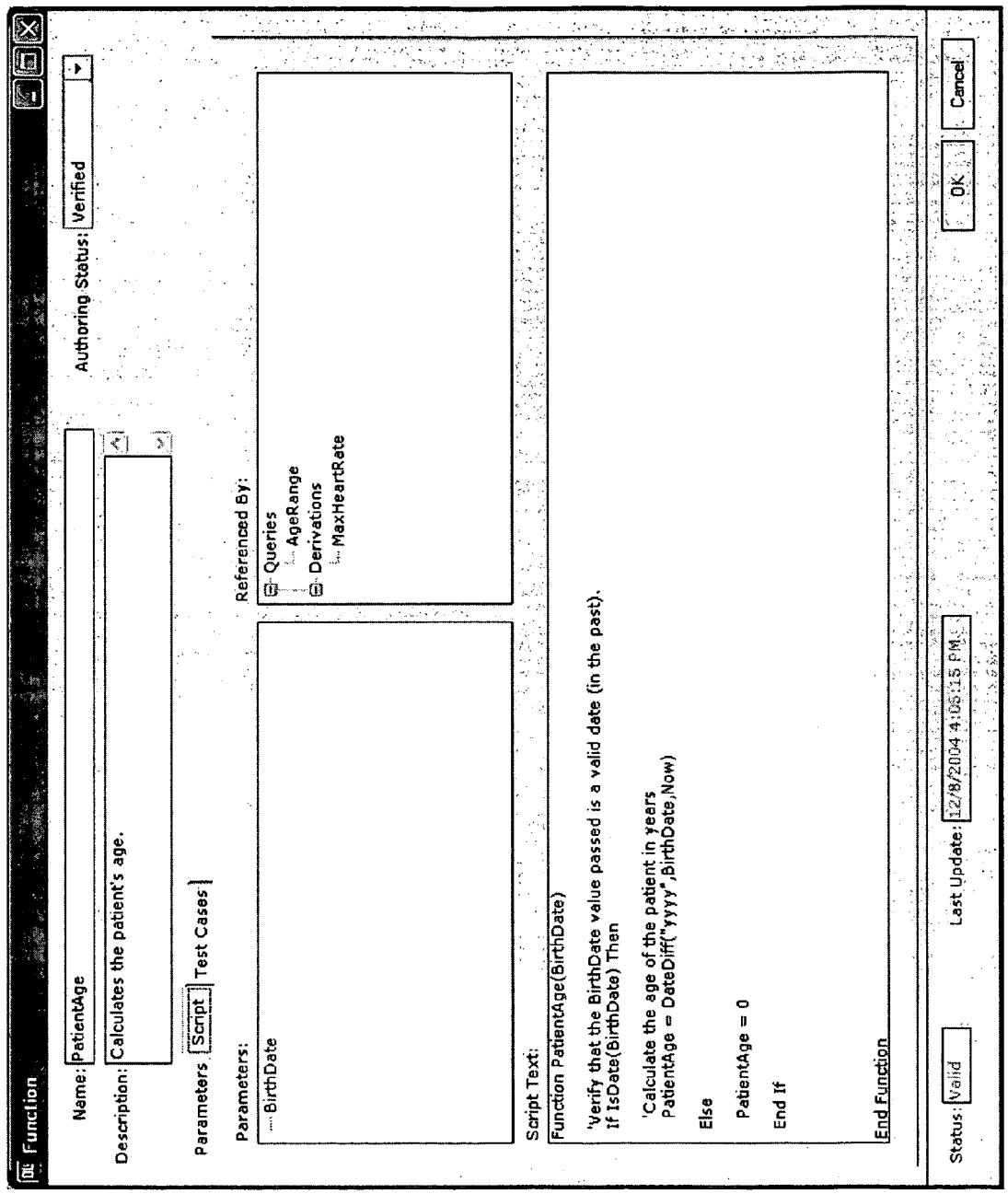
Figures 2, 8N:
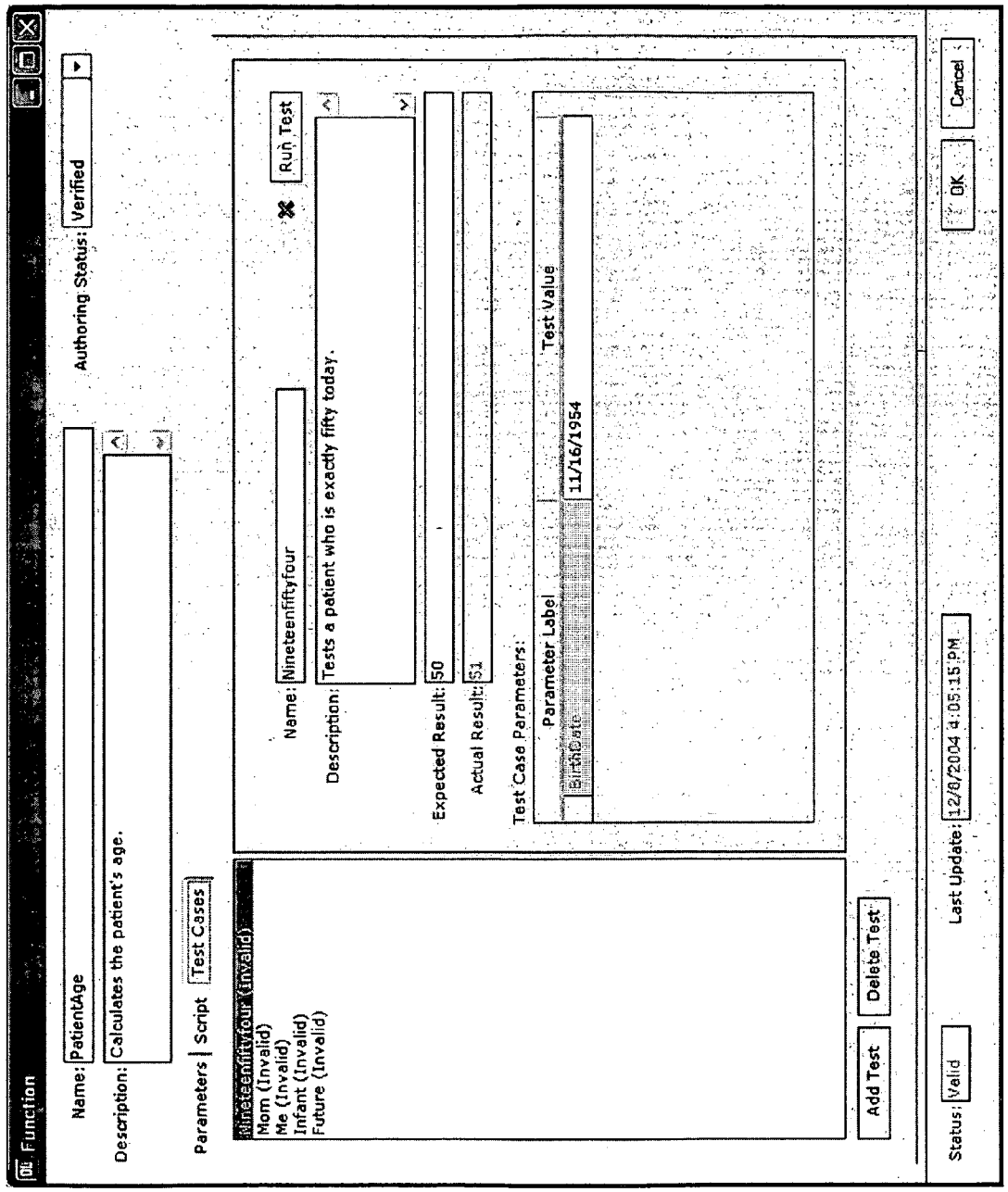
Figures 1, 8O:
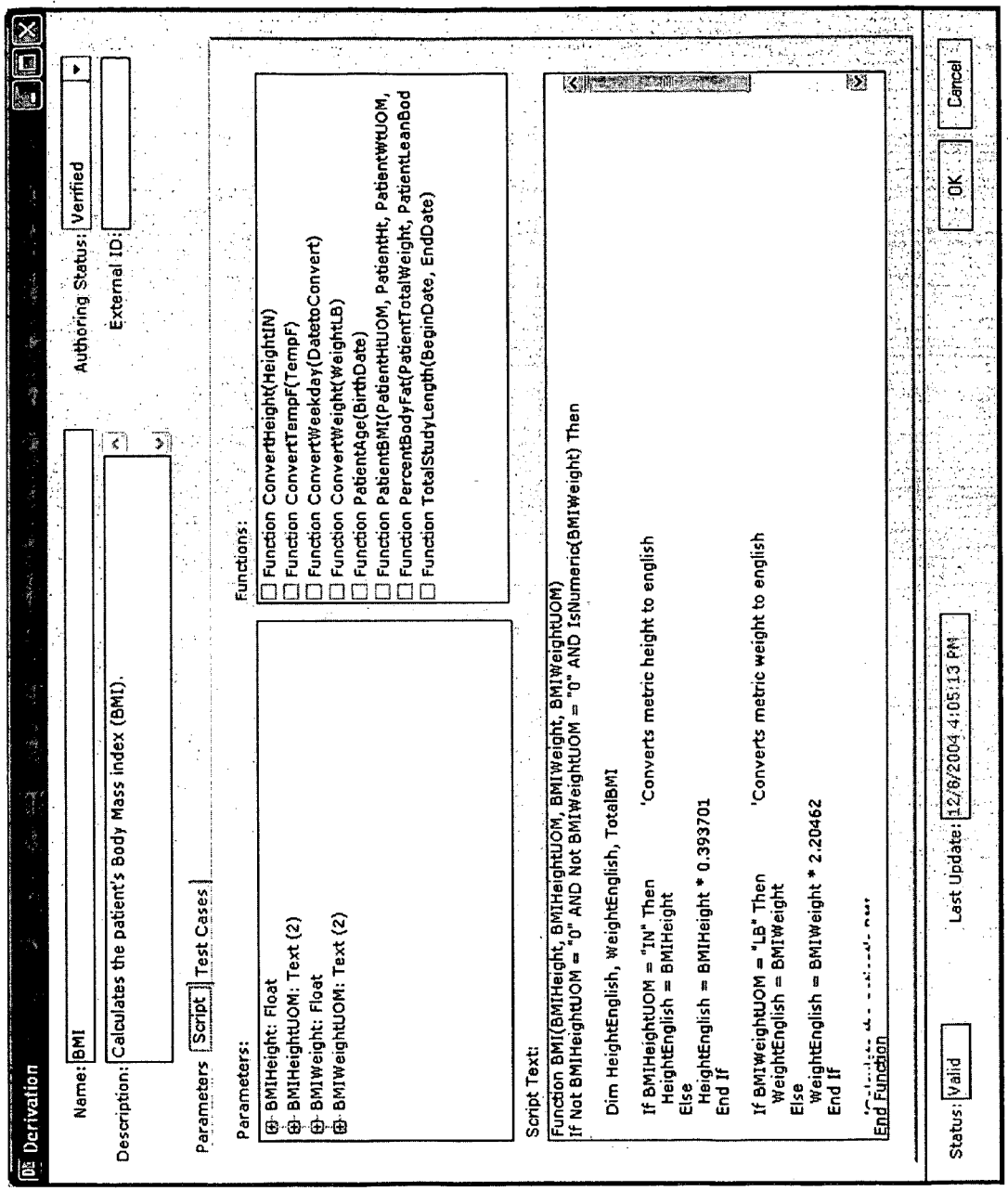
Figure 8P:
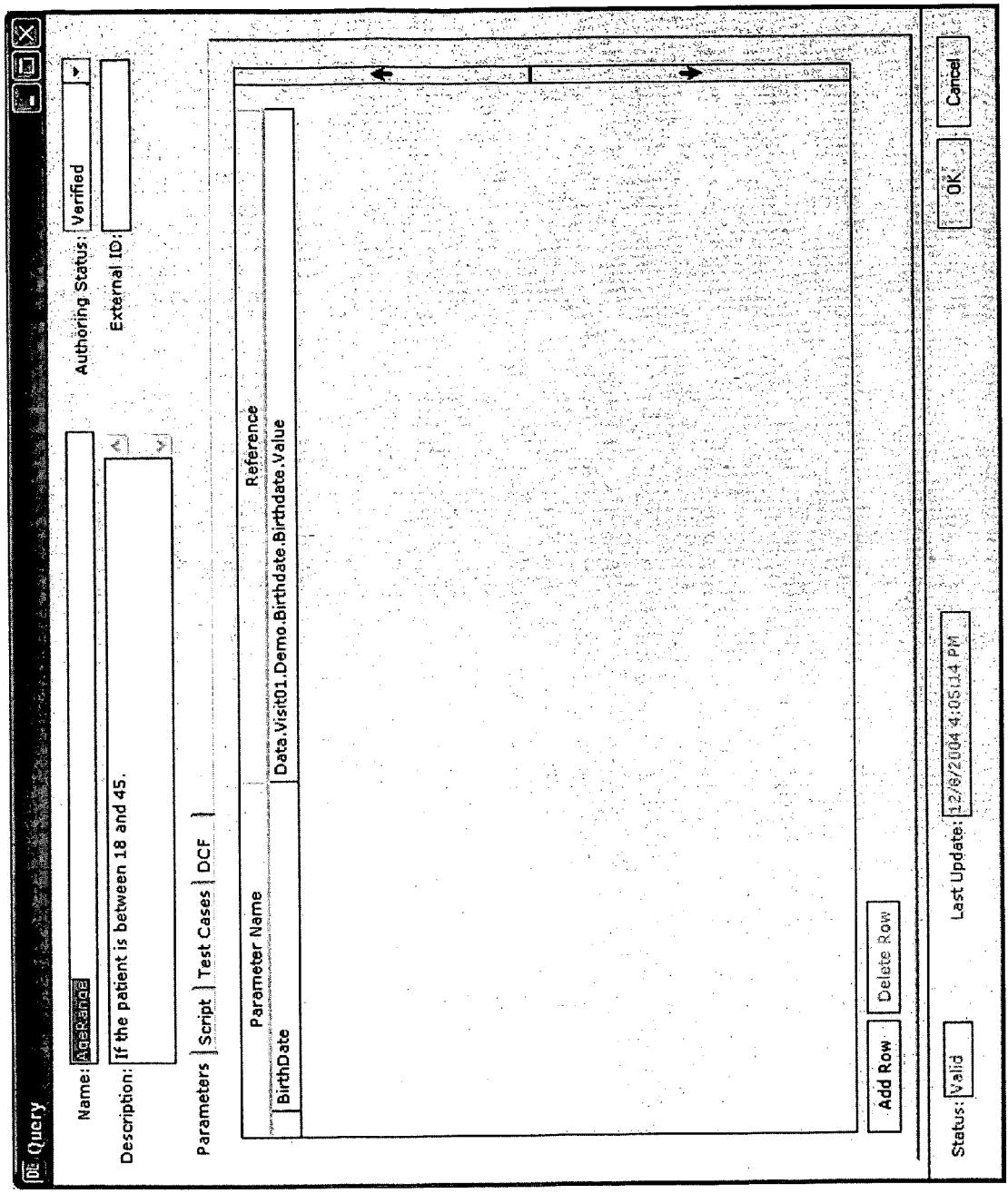
Figures 1, 8P:
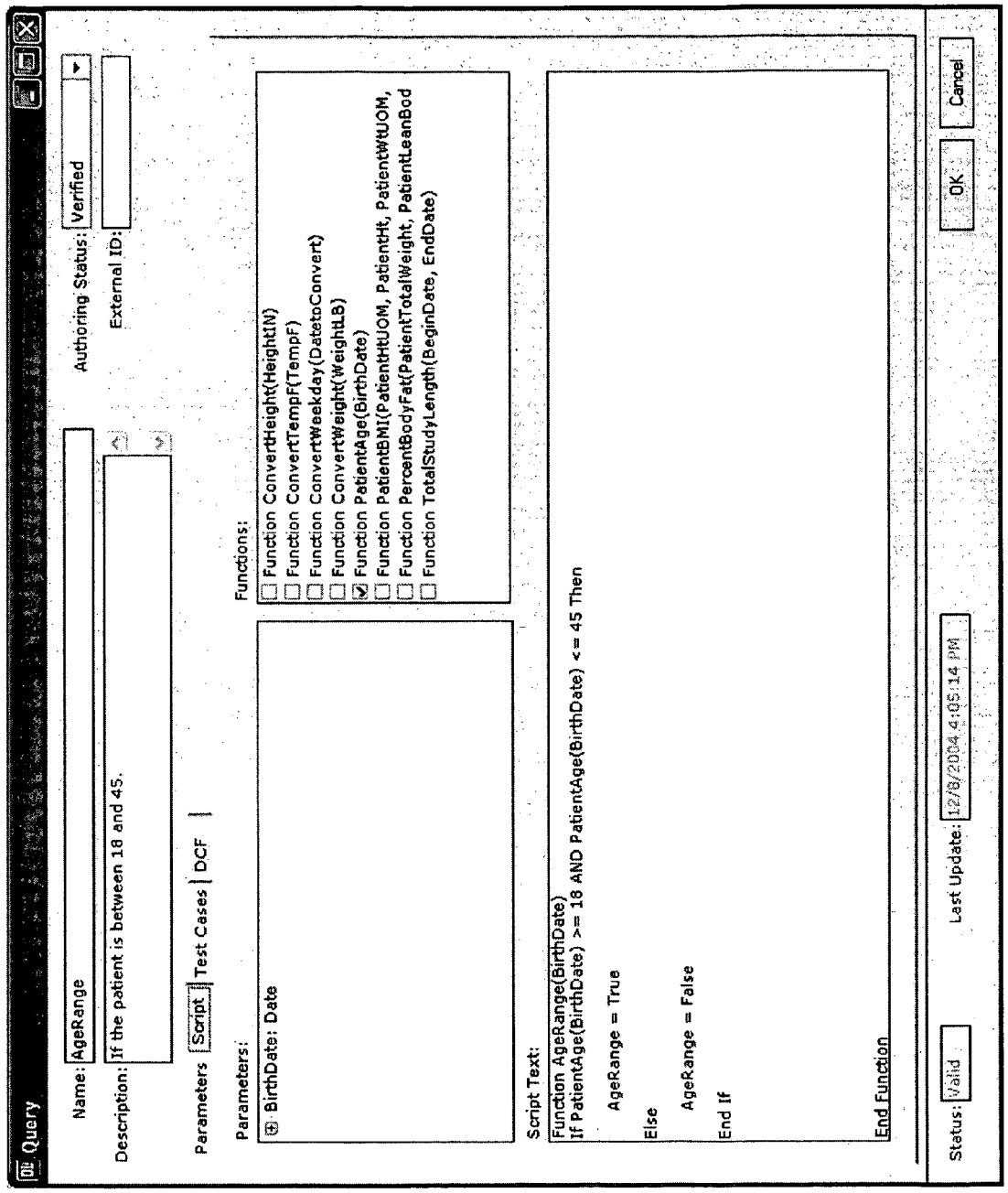

Referring now to FIG. 2, Table 200 illustrates a name and corresponding description of embodiments of exemplary visual cues or mechanisms of the designer program 108. As shown in FIG. 2, the visual shapes 202 represent, among other possibilities, components of a clinical trial. By organizing trial components into shapes capable of simple drag-and-drop, double-click select, or the like, the designer program 104 advantageously reduces often complex functionality to easily understandable and editable shapes. Accordingly, users of the designer program or tool 104 can be less technically skilled than the typical programmers and database designers used for customizing systems for particular protocols. In addition, the less technically skilled users of the designer program 108 often can design a protocol and implement it on the clinical trial program 100 faster than the foregoing programmers and database designers using conventional customization methods. FIGS. 8A through 8P-3 will be referenced to illustrate the Properties for each shape that are mentioned throughout this section.

As shown in FIG. 2, the shapes 202 may include a Study shape used, for example, to define such things as study name, study description, protocol number, protocol description and the like. (FIG. 8A illustrates an exemplary screen view of Study Shape Properties). The shapes 202 may also include a Path shape used, for example, to define a unique patient pathway (i.e. sequence of patient events). The Path Shape properties store such things as path name, path display name, whether or not the path is the default pathway, and the like (FIG. 8E illustrates an exemplary screen view of Path Shape Properties). The shapes 202 may also include a Form shape, used for example, to define such things as form name, form display name, whether it can be used within an unscheduled event, and the like. In an embodiment, Forms are commonly referred to as Case Report Forms (CRF), which represent a single form of a Case Book. (FIG. 8C illustrates an exemplary screen view of Form Shape Properties). The shapes 202 may also include a Common Event shape used, for example, to define such things as event display name, display order (i.e. first or last), associated forms, and the like. The Common Event is used to display forms that are not associated to a particular patient visit. (FIG. 8D illustrates an exemplary screen view of Common Event Shape Properties).

The shapes 202 may also include an Event shape used, for example, to define such things as event name, event order, associated forms, and the like. In addition, event minimum, ideal, and maximum event windows may be defined based on previous event dates (FIGS. 8F and 8F-1 illustrate an exemplary screen view of Event Shape Properties). In an embodiment, events are also commonly known as visits.

The shapes 202 may also include a Patient State shape used, for example, to define the different patient statuses that a patient can obtain through the course of the study. Patient State shape properties store such things as patient state display name, associated icon, action display name, column header display name, and the like (FIG. 8B illustrates an exemplary screen view of Patient State Shape Properties). The shapes 202 may also include Patient State Transition shapes used, for example, to connect the Patient State shapes in a manner that defines what patient state a patient can transition to from a previous state.

The shapes 202 may also include Group shapes used, for example, to define a listing of data items. The Group Shape properties store such things as group name and domain reference along with one or more data items that comprise a name, data type, code list reference, min/max length, min/max precision, derivation reference, dictionary reference, comments, and the like (FIG. 8H illustrates an exemplary screen view of Group Shape Properties). Data items describe the physical data points that are collected during a trial. The shapes 202 may also include Domain shapes used, for example, to define logical categories that are used to organize groups for the purpose of reporting and data exports. The domain shape properties store the name of the domain, and the like (FIG. 8I illustrates an exemplary screen view of Domain Shape Properties). The shapes 202 may also include CodeList shapes used, for example, to define value pairs that ultimately can be referenced by a data item. The value pairs comprise a display value and a stored value. In addition, the default value pair is designated. CodeList shape properties store such things as code list name, value pairs, and the like (FIG. 8J illustrates an exemplary screen view of CodeList Shape Properties). The shapes 202 may also include Dictionary shapes used, for example, to define dictionaries that ultimately can be referenced by data items for the purpose of encoding. The Dictionary Shape Properties store such things as dictionary name, type, version, and the like (FIG. 8G illustrates an exemplary screen view of Dictionary Shape Properties).

The shapes 202 may also include Question shapes used, for example, to define the individual fields that are displayed on the form for the purpose of capturing data from the user. Question shapes can be dropped directly on the form or within a table shape. Question shape properties store such things as question name, display order, question display prompt, data item reference and conditional logic. In addition, data validations can be turned on to check such things as data type, min/max length, min/max precision, defined range, and the like (FIGS. 8K through 8K-2 illustrate exemplary screen views of Question Shape Properties). The shapes 202 may also include Table shapes used, for example, to define a table of repeating row questions. Question shapes can be dropped within the table and ordered to define the columns of data to be captured within the table. Table properties store such things as table name, display order, table display prompt, and the like (FIG. 8M illustrates an exemplary screen view of Table Shape Properties). The shapes 202 may also include Info shapes used, for example, to define text and graphics to be displayed on the form along with optional tags, such as HTML tags, that can be used to format the text (FIG. 8L illustrates an exemplary screen view of Info Shape Properties).

The shapes 202 may also include Derivation shapes used, for example, to define logic for the purpose of deriving a value from one or more variables that ultimately can be associated to a data item. Derivation shape properties store such things as derivation name, description, parameter references, script, test values, and the like (FIG. 8O illustrates an exemplary screen view of Derivation Shape Properties. In addition, FIGS. 8O-1 and 8O-2 illustrate exemplary screen views of the Script and Test Cases sub-tabs, respectively). The shapes 202 may also include Query shapes used, for example, to define logic for the purpose of evaluating one or more variables to determine a True or False response. Query shape properties store such things as query name, description, parameter references, script, test values, default data clarification form settings, and the like (FIG. 8P illustrates an exemplary screen view of Query Shape Properties. In addition, FIGS. 8P-1, 8P-2, and 8P-3 illustrate exemplary screen views of the Script, Test Cases, and DCF sub-tabs, respectively.). The shapes 202 may also include Function shapes used, for example, to define logic to be referenced by a script within a derivation or query shape. Function shape properties store such things as function name, description, parameter references, script, test values, and the like (FIG. 8N illustrates an exemplary screen view of Function Shape Properties. In addition, FIGS. 8N-1 and 8N-2 illustrate exemplary screen views of the Script and Test Cases sub-tabs, respectively).

Specific examples of many of the foregoing shapes are further highlighted and described with reference to FIGS. 5, and 6A through 6P. Moreover, a skilled artisan will recognize other trial components, including complex or layered trial components that can advantageously be reduced to shapes, visual cues or mechanisms or the like that allow for easy manipulation and customizations. Although disclosed with reference to preferred and alternative embodiments, an artisan will recognize from the disclosure herein a number of other visual cues and/or other trial components that can be represented by the visual cues. For example, the visual cues may include pull down menus, radio buttons providing available selections, selection boxes, sub-windows, sub-tabs, tool boxes, tool bars, combinations of the same, or the like.

FIG. 3 is a block diagram illustrating documents and their interrelationships used by the designer program 108, according to an embodiment of the invention. As shown in FIG. 3, a data store 302 includes the clinical study design, which in the disclosed embodiment is represented to the designer/user via several disparate documents. Once the study design is completed in the designer program 108, configuration files 106 representing the study design are uploaded into the clinical trial program 100, as stated above, where the protocol of the actual clinical trial is carried out based upon the "instructions" defined within the configuration files 106.

Figure 4:
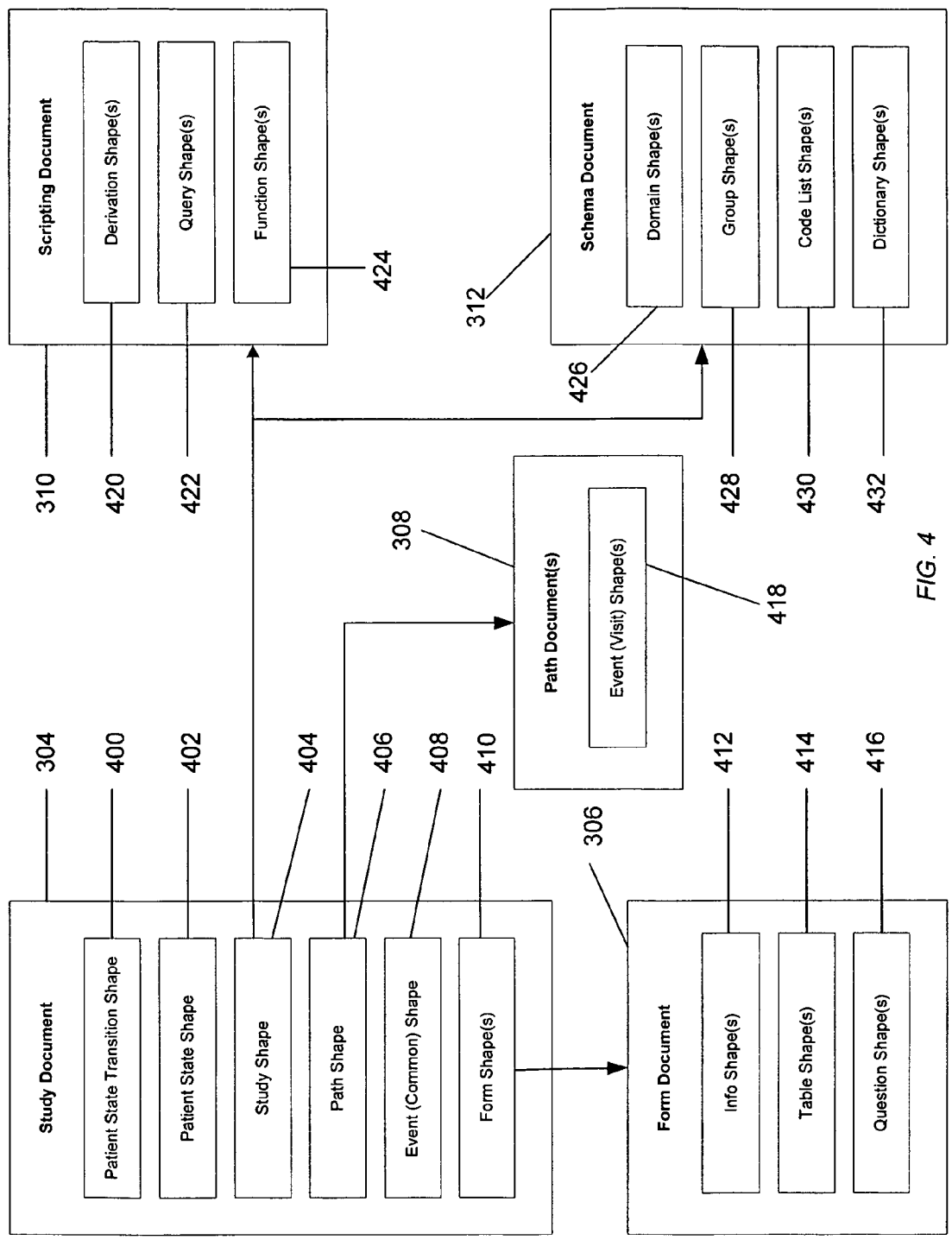
FIG. 4 is a dependency diagram further highlighting the documents along with their associated shapes and interrelationships with other documents and shapes.

In an embodiment, the study design is broken down into document types or windows that comprise one or more shapes, such as, for example, the shapes defined with reference to FIG. 2 and/or their organization disclosed with reference to FIG. 4. When a shape is added to a document, or properties are changed for a particular shape, the instructions (i.e., the data store 302) are updated. Each document includes a stencil which comprises a collection of shapes that can be used with that document. Study document 304, which stores data in the data store 302 comprises the master document and maintains the relationships with all other documents. The study document 304 can be used to define study properties, forms, common forms, paths (i.e., patient regimen), and patient workflow.

A form document 306, which stores data in the data store 302, is generated by the system for each patient state defined within the study document workflow page and for each form defined within the study document forms page. A form document 306 can advantageously be used to define what is presented to the clinical trial participant or user when opening that particular form via the clinical trial program 100, which can include, among other things, text and fields for the purpose of collecting data as part of the clinical trial. In addition, certain logic can be defined to adjust the display of the form or run certain checks depending on what is entered by the user.

A path document 308, which stores data in the data store 302, is generated by the system for each path defined within the study document regimen page. A path document 308 can be used to, among other things, define a sequence of patient visits for a particular path including those forms that are to be collected at each visit.

A scripting document 310, which stores data in the data store 302, is used to define logic that is run against the data that is entered as part of the clinical trial. The logic can be straightforward or quite complex. The study document 304 can support at least the following two primary logic types: queries and derivations. Queries are used to evaluate data as it is entered by the user and depending on the results, trigger an action, most commonly the generation of a data clarification request. Derivations are used to derive other fields based on data entered by the user or those that are already in existence within the system. In addition, functions can be defined which comprise predefined logic that can be referenced by a query or derivation.

A schema document 312, which stores data in data store 302, can be used to define the data items that can be referenced within a form. Data items are organized within groups and each group is associated to a domain. Individual data items may reference a code list, derivation, or dictionary.

Referring now to FIG. 4, an amplification of the above-described documents is shown in a dependency diagram illustrating organization of the documents and shapes with respect to one another. The Study Document 304 is shown to comprise a Study shape 404 which is automatically added by the system and cannot be deleted by the user. The study shape maintains association with the schema document and scripting document.

Patient State shape(s) 402, which are used to define the different patient statuses that a patient can obtain through the course of a study along with the Patient State Transition Shape(s) 400, which are used to connect the patient state shapes in a manner that defines what patient state a patient can transition to from a previous state.

Path shape(s) 406, which are used to define a unique patient pathway (i.e. sequence of patient visits). When a new path shape is dropped on the page, a corresponding path document is generated by the system.

Event (Common) shape 408, which is a special event shape that is automatically added by the system and cannot be deleted by the user. The common event shape maintains the relationship with forms that are not associated to a particular patient visit (i.e. Event Shape).

Form shape(s) 410, which ultimately can be associated to one or events, are used to define each unique form that may be used within the study. When a new form shape is dropped on the page a corresponding form document is generated by the system.

The Form Document(s) 306 is shown to comprise Info shape(s) 412, which are used to display free form text and graphics on a form. Info shapes can be ordered with respect to other shapes on the form document.

Table shape(s) 414, which are used to define a table of repeating row questions. Question shapes (referred to below) can be dropped within the table and ordered to define the columns of data to be captured within the table. Table shapes can be ordered with respect to other shapes on the form document.

Question shape(s) 416, which ultimately can be associated to one or more data items, are used to define the individual question and field (i.e. data item) pairs that are displayed on the form for the purpose of capturing data from the user. Question shapes can be dropped directly on the form or within a table shape. Question shapes dropped outside of a table can be ordered with respect to other shapes on the form document.

The Path Document(s) 308 is shown to comprise a single set of shapes, the Event shape(s) 418, which are used to define the patient events (i.e. patient visits), their sequence and the forms that are to be collected at each event.

The Scripting Document 310 is shown to comprise Derivation shape(s) 420, which ultimately can be associated to one or more data items, are used to define logic for the purpose of deriving a value from one or more variables, typically data items referenced by a question shape.

Query shape(s) 422, which are used to define logic for the purpose of evaluating one or more variables, typically data items referenced by a question shape, to determine a True or False response.

Function shape(s) 424, which are used to define logic to be referenced by a script within a Derivation 420 or Query 422 shape.

The Schema Document 312 is shown to comprise Domain shape(s) 426, which ultimately can be associated to one or more group shapes, are used to organize groups for the purpose of reporting and data exports.

Group shape(s) 428, which are used to define a listing of data items.

Code List shape(s) 430, which ultimately can be associated to one or more data items, are used to define a set of display and stored value pairs.

Dictionary shape(s) 432, which ultimately can be associated to one or more data items, are used to define dictionaries for the purpose of encoding.

Although FIGS. 3 and 4 are disclosed with reference to preferred implementations and embodiments, a skilled artisan will recognize from the disclosure herein a wide number of alternative organizational schemes for organizing how a designer/user interacts with the visual cues, or shapes, to customize the clinical trial program 100 to particular protocols for particular clinical trials.

Figure 5:
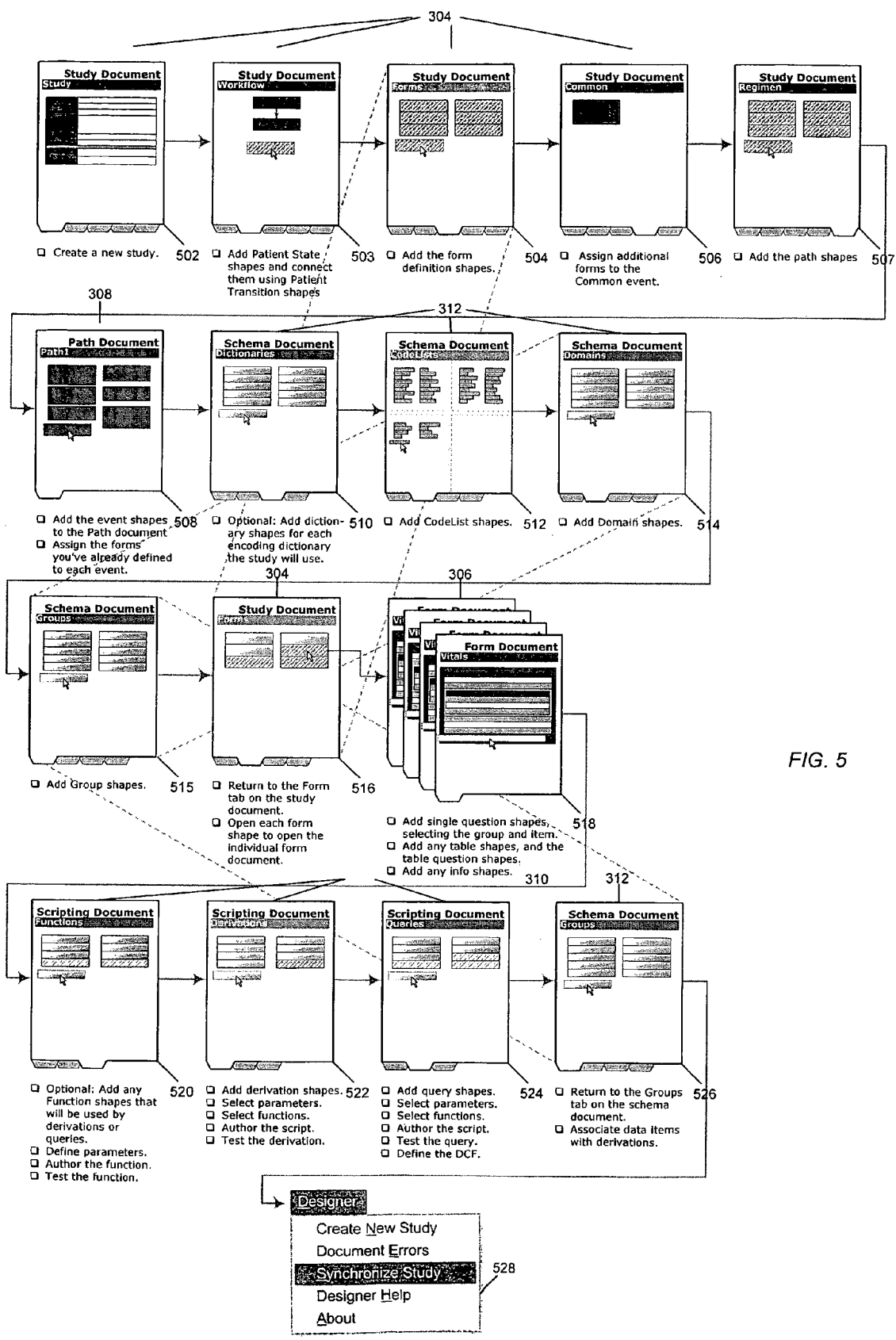
FIG. 5 is a data flow diagram illustrating an exemplary application of the designer program of FIG. 1 to a simplified protocol in order to configure a clinical trial program.

FIG. 5 forms a data flow diagram illustrating an exemplary application of the designer program 108 of FIG. 1 to a simplified protocol in order to configure the clinical trial program 100. For example, to better illustrate the functionality and straightforwardness of the present designer program 108, FIG. 5 illustrates potential design actions a designer/user may perform to customize the clinical trial program 100 using the designer program 108 for a highly simplified clinical trial protocol. For example, FIG. 5 illustrates Block 502 where a designer creates a new clinical trial or study and can fill in general data in the Study Shape properties screen. By selecting a "Workflow" tab at block 503, the designer may populate the Study Document 304 with Patient State shapes and connect them using Patient State Transition shapes. By selecting a "Forms" tab at Block 504, the designer may populate the Study Document 304 with Form shapes by, for example, dragging-and-dropping one or more Form shapes from a stencil. Moreover, by selecting a "Common" tab at Block 506, the designer may change properties of the Common event shape. These changes may include association with the foregoing populated forms and selecting whether the common event will display first or last.

At Block 507, the designer may select a "Regimen" tab and populate the Study Document 304 with Path shapes by, for example, dragging-and-dropping one or more Path shapes from a stencil. At Block 508, the designer may change to the Path Document 308 and layout a basic or complex workflow definition governing the order of particular events (such as, for example, Visit 1, Visit 2, etc.) defined in the protocol of the clinical trial. The designer may define the flow, by, for example, dragging-and-dropping one or more Event shapes from a stencil into the Path Document 308. In an embodiment, the designer may advantageously order the events or create a flowchart or data flow diagram to define the workflow events, including, for example, associating the foregoing populated forms with particular events in the workflow. Use of the Event shapes allows the designer to, for example, define dependencies between events and other events, forms, or the like.

At Block 510, the designer may change to the Schema Document 312, select a "Dictionaries" tab and populate the Schema Document 312 with Dictionary shapes by, for example, dragging-and-dropping them from a stencil. In an embodiment, the Dictionary shapes define each encoding dictionary for the clinical trial. Encoding dictionaries advantageously allow automatic encoding of various entries for the trial. Moreover, a dictionary may define official diagnoses and/or specific alphanumeric codes for those diagnoses.

In an embodiment, any one or more of the shapes may change their visual appearance to indicate, for example, whether the designer has customized the properties of a particular shape, whether the shape is sufficiently defined or data items therein sufficiently resolved, whether particular codes are available, or the like. For example, the shapes may change the darkness thereof, may change from red or yellow to green, or the like.

At Block 512, the designer may select a "CodeLists" tab and populate the Schema Document 312 with CodeList shapes by, for example, dragging-and-dropping them from a stencil. In an embodiment, the CodeList shapes define, for example, appropriate data entries for specific questions. For example, to a question on sex, the CodeList may define "M" and "F." At Block 514, the designer may select a "Domains" tab and populate the Schema Document 312 with Domain shapes by, for example, dragging-and-dropping them from a stencil. In an embodiment, Domain shapes define a set of related groups. At Block 515, the designer may select a "Groups" tab and populate the Schema Document 312 with Group shapes by, for example, dragging-and-dropping them from a stencil. In an embodiment, the Group shapes define a set of related data items.

At Blocks 516 & 518, the designer may revert back to the Study Document 304, select the "Forms" tab and customize each of the individual Form documents associated with the foregoing Form shapes or add/remove additional shapes. The customization of each Form Document 306 can include the addition of Question shapes, Table shapes, Information shapes, or the like by, for example, dragging-and-dropping them from a stencil.

At Block 520, the designer may change to the Scripting Document 310, select a "Functions" tab and populate the Scripting Document 310 with Function shapes by, for example, dragging-and-dropping them from a stencil. In an embodiment, the Function shapes define parameters and/or author a script (such as, for example, in VBScript) that can be used in derivations, queries, or the like. According to an embodiment, the Functions tab of the Scripting Document 310 may include the ability to validate some or all of the programmed functions. For example, the Functions tab may include positive and negative tests where hypothetical data may be entered during design, and the positive and negative tests examined to ensure proper functionality before implementation by the clinical trial program 100. Thus, the designer may advantageously define the appropriate parameters for a Function shape, author the functionality, and test hypothetical results to ensure proper performance of the functionality.

At Block 522, the designer may select a "Derivations" tab and populate the Scripting Document 310 with Derivation shapes by, for example, dragging-and-dropping them from a stencil. In an embodiment, the Derivation shapes define, for example, replacement data as a substitute for data actually entered. For example, the Derivation shapes may employ an entered AGE and YEARS AFFLICTED, and produce an AGE AFFLICTED entry. According to an embodiment, the designer may advantageously define the appropriate parameters for a Derivation shape, select appropriate functions, author a script (for example, as in VBScript), test hypothetical results, and the like.

At Block 524, the designer may select a "Queries" tab and populate the Scripting Document 310 with Query shapes by, for example, dragging-and-dropping them from a stencil. In an embodiment, the Query shapes define, for example, rules that may request a clarification from, for example, a data entry user. According to an embodiment, the designer may advantageously define the appropriate parameters for a Query shape, select appropriate functions, author a script (for example, in VBScript), test hypothetical results, define the clarification requests, and the like.

At Block 526, the designer may revert back to the Schema Document 312 and resolve any data items with unassigned properties (such as, for example, a reference to a derivation). As disclosed in the foregoing, the unresolved shapes may be colored to show whether resolution still needs to occur. For example, shapes needing resolution may be red, yellow, or the like, while shapes completely resolved may advantageously be green.

At Block 528, the designer used the designer program 108 to efficiently and non-technically create or customize a protocol for a clinical trial. The designer simply selects the Synchronize Study option and after testing the design for errors the configuration file 106 is prepared, ready to be uploaded to the clinical trial program 100, and a fully tested and customized clinical trial can be started. For example, the testing was accomplished during the foregoing function, derivation and query design phases, the forms were designed and entered, the workflow was designed and entered, and the configuration files 106 were uploaded to properly configure and define the backend database system 104.

While the foregoing design actions of a designer/user have been disclosed with reference to certain preferred and alternative embodiments, an artisan will recognize from the disclosure herein that a designer may employ the designer program 108 in a wide variety of ways to make the design of a particular protocol highly reusable and scalable. For example, libraries of designs and template designs may be stored that define the basics of one or more common protocols and the designer may advantageously only customize small portions of the trial. Additionally, other combinations, omissions, substitutions and modifications will be apparent to the skilled artisan in view of the disclosure herein.

Figure 6A:
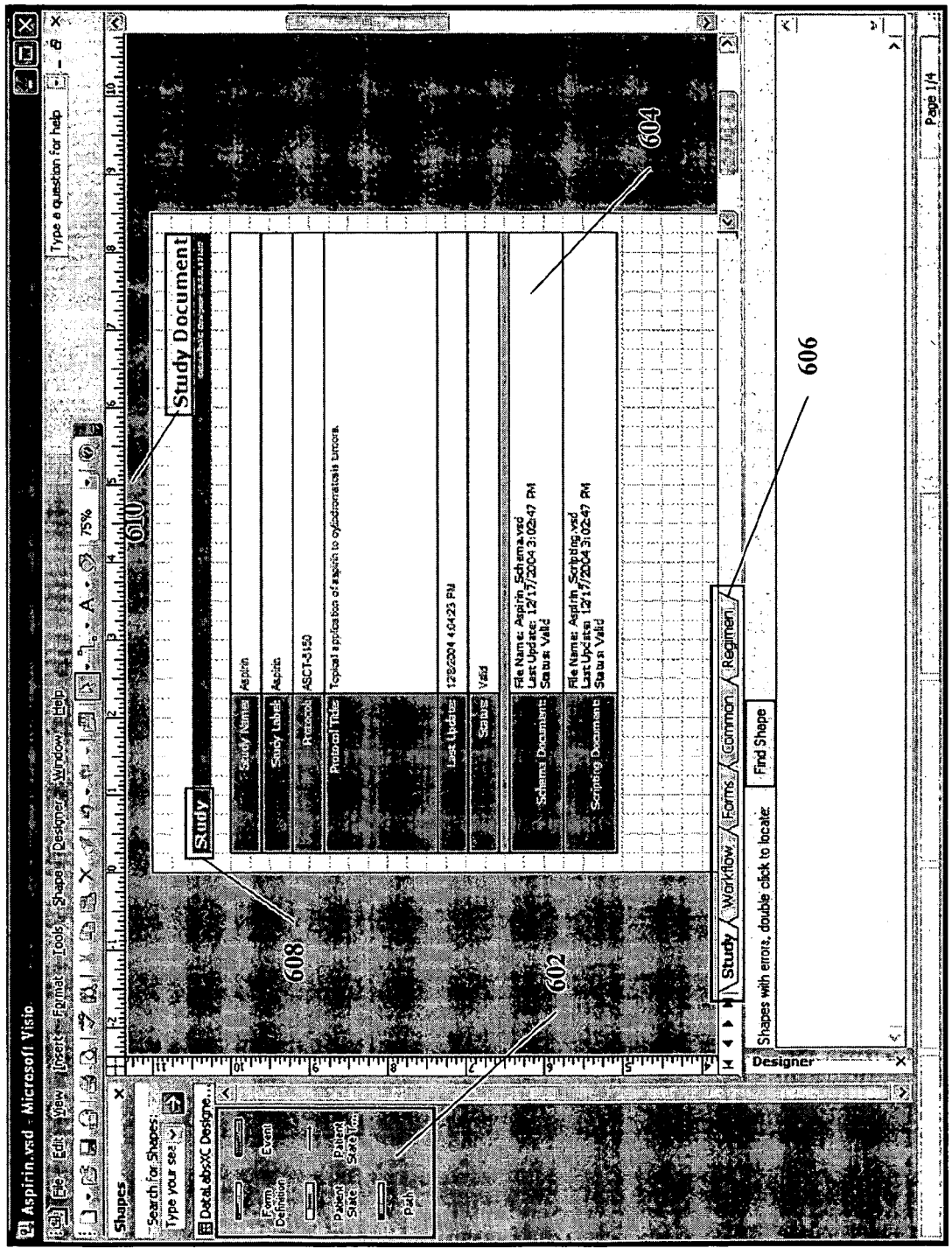
FIGS. 6A through 6P are exemplary simplified screen views illustrating embodiments of the designer program as it is applied in FIG. 5.
Figure 6B:
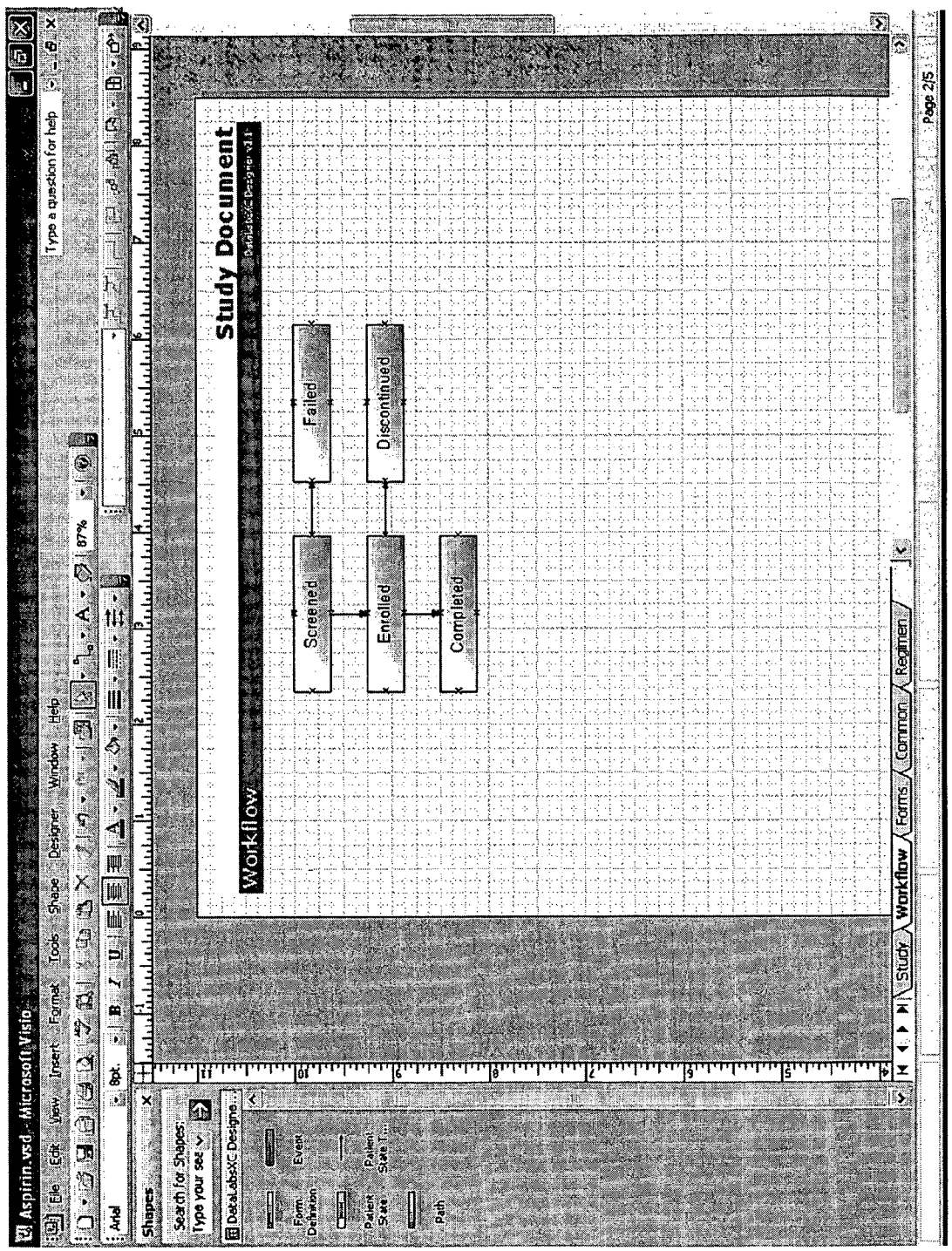
Figure 6C:
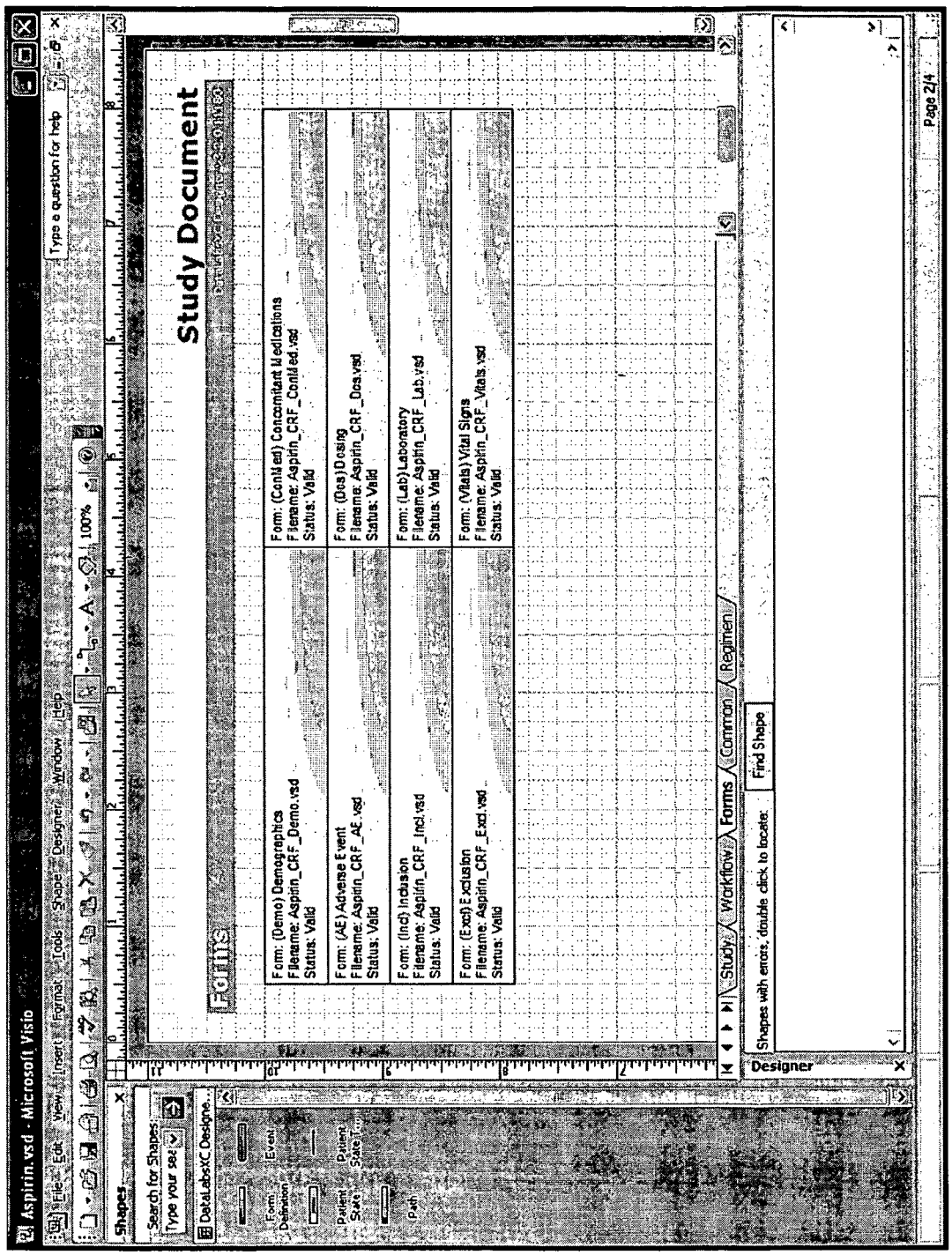
Figure 6D:
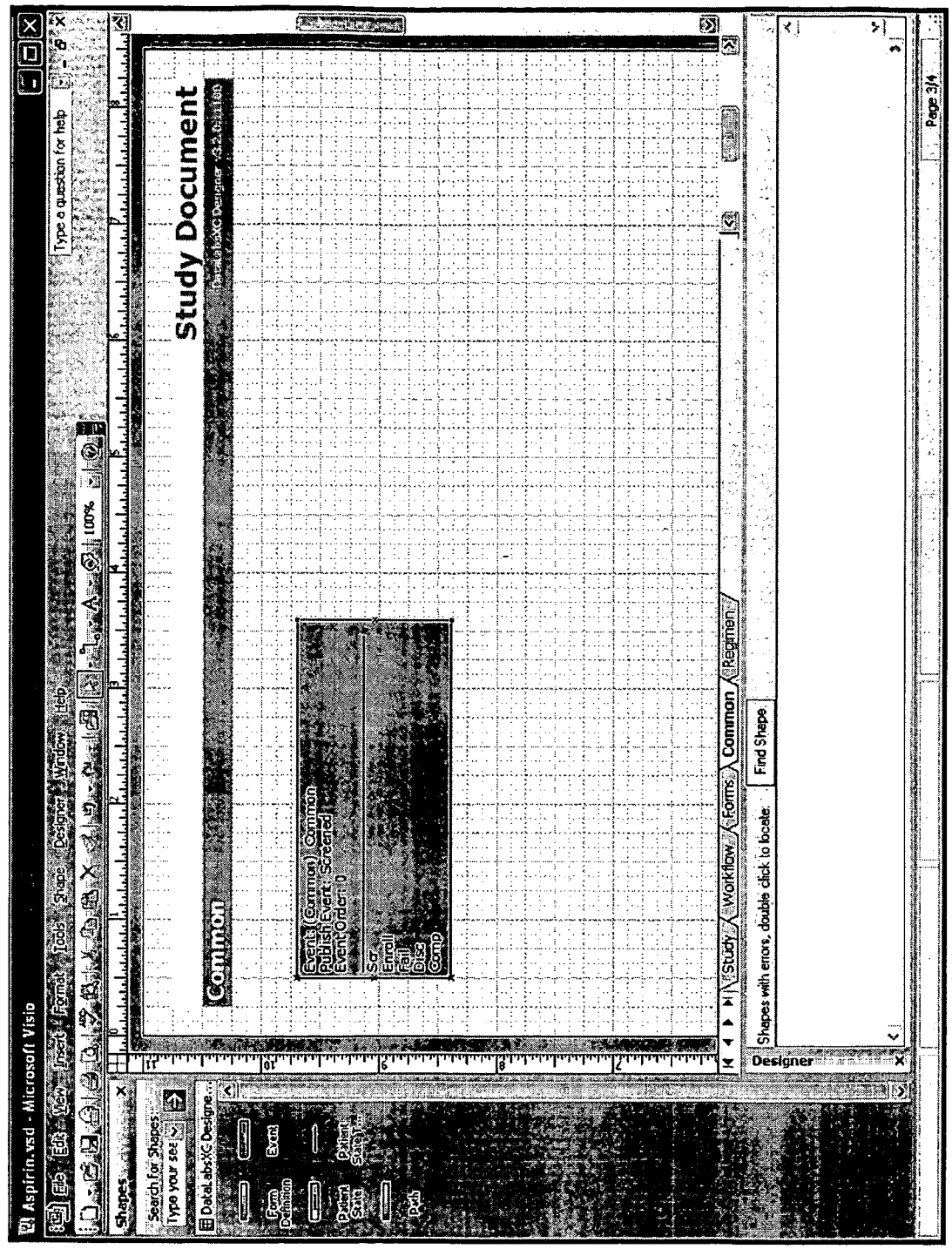
Figure 6E:
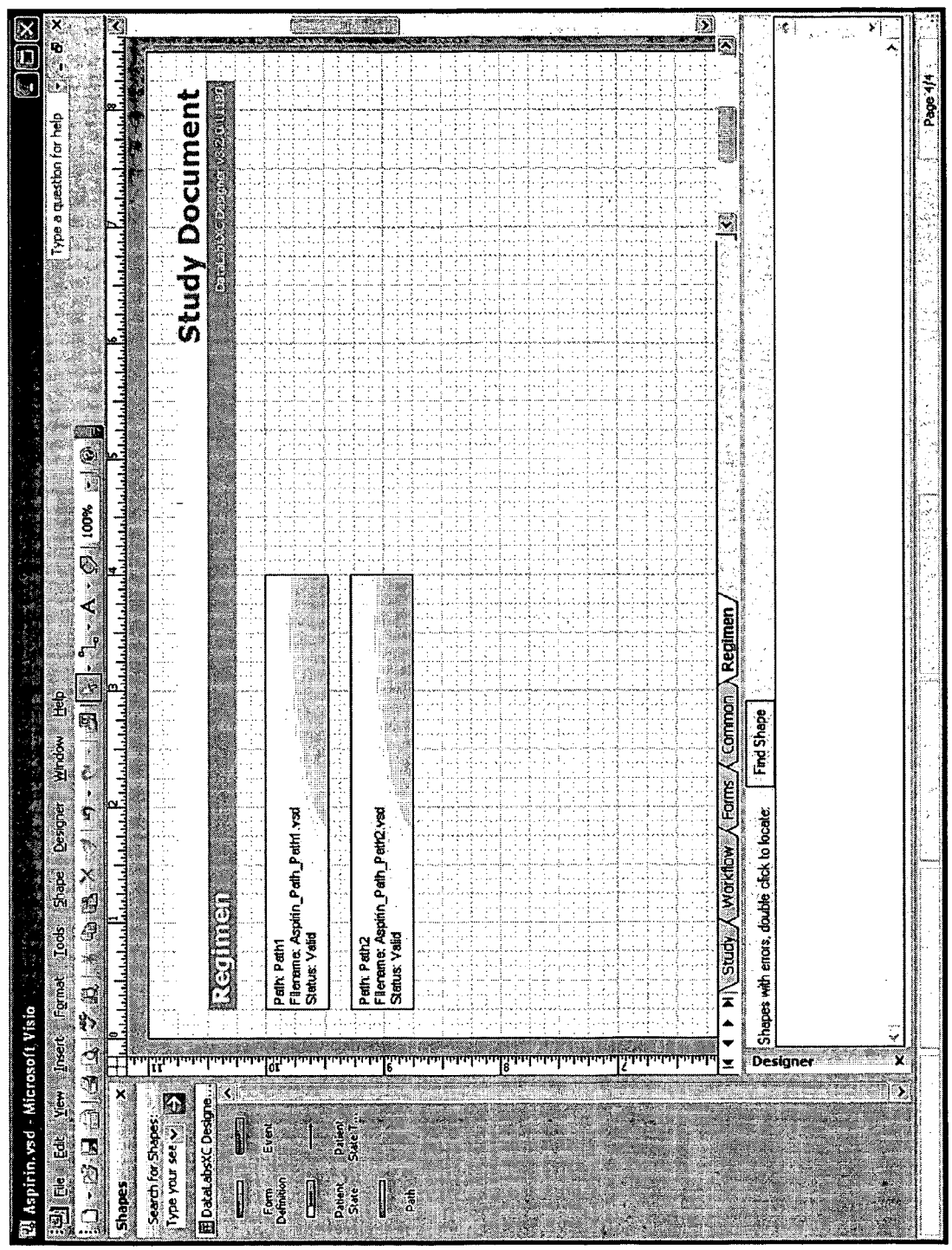
Figure 6F:
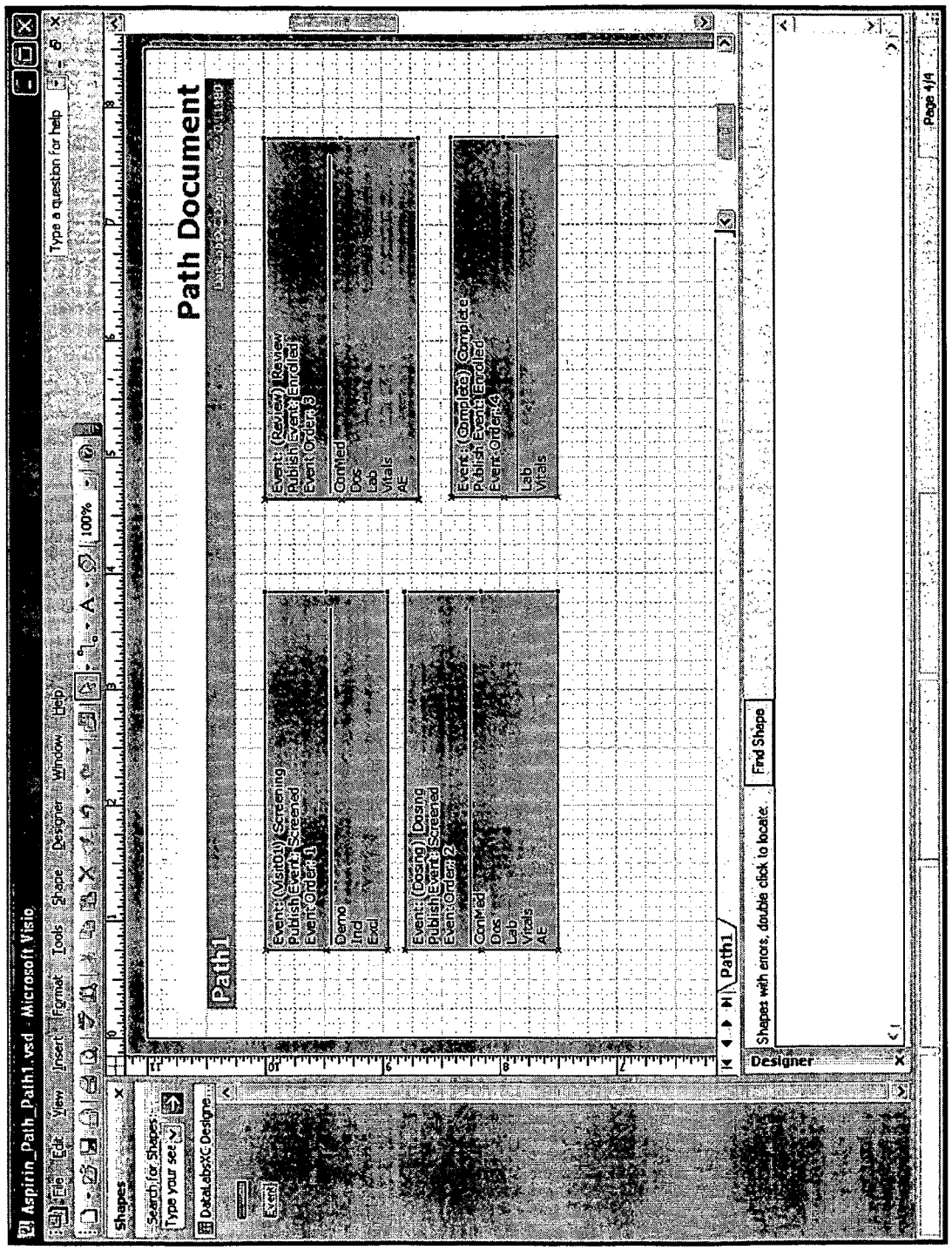
Figure 6G:
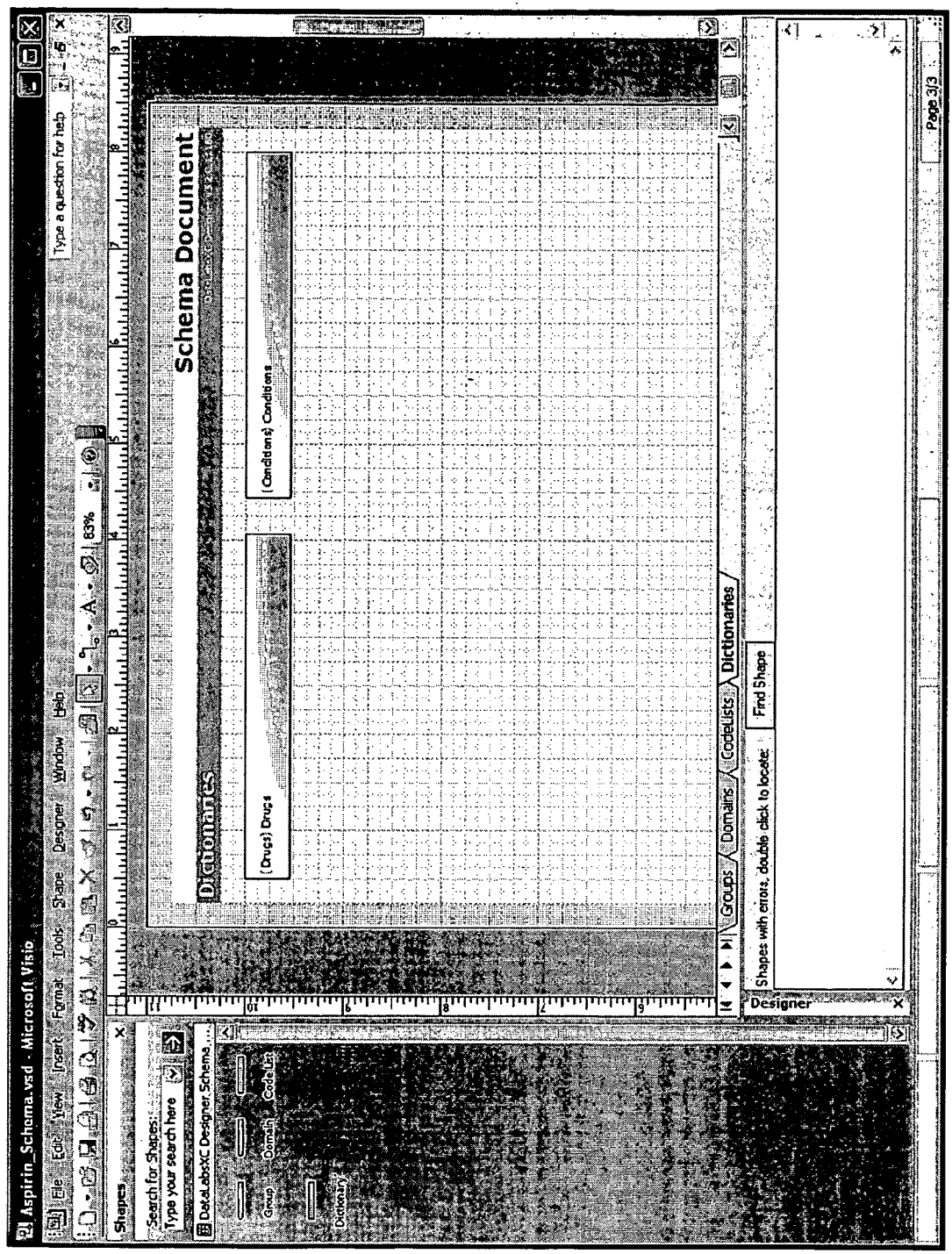
Figure 6H:
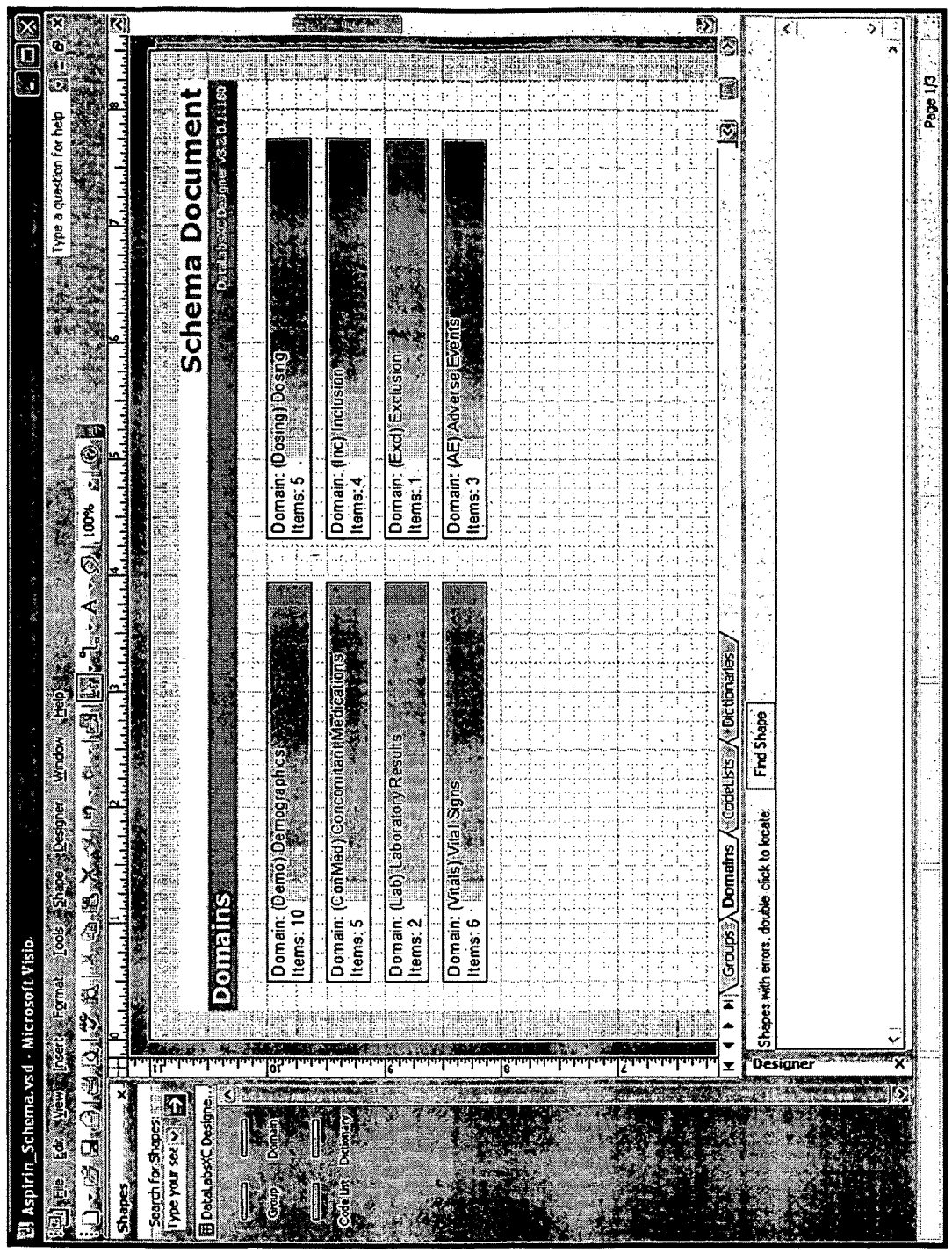
Figure 6I:
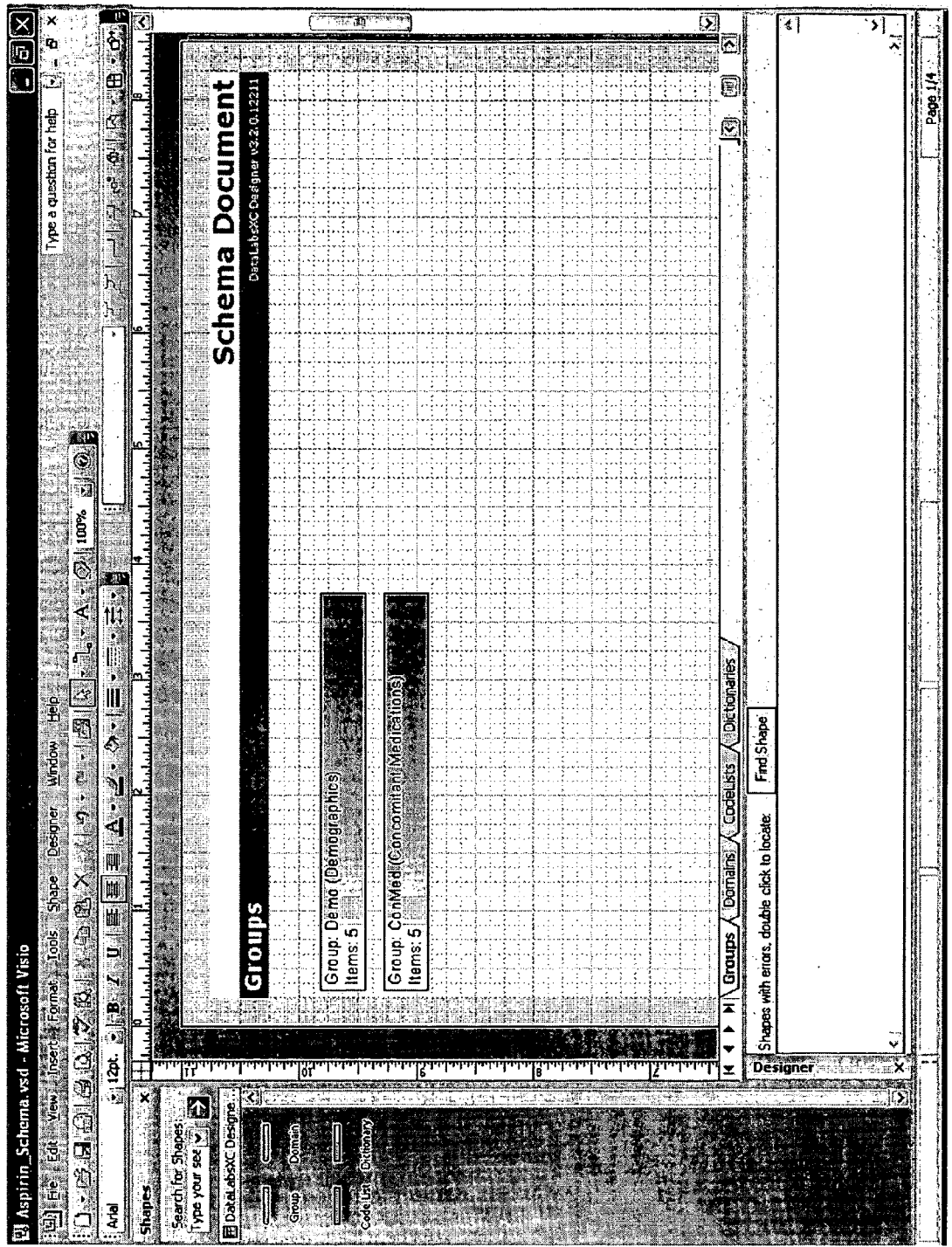
Figure 6J:
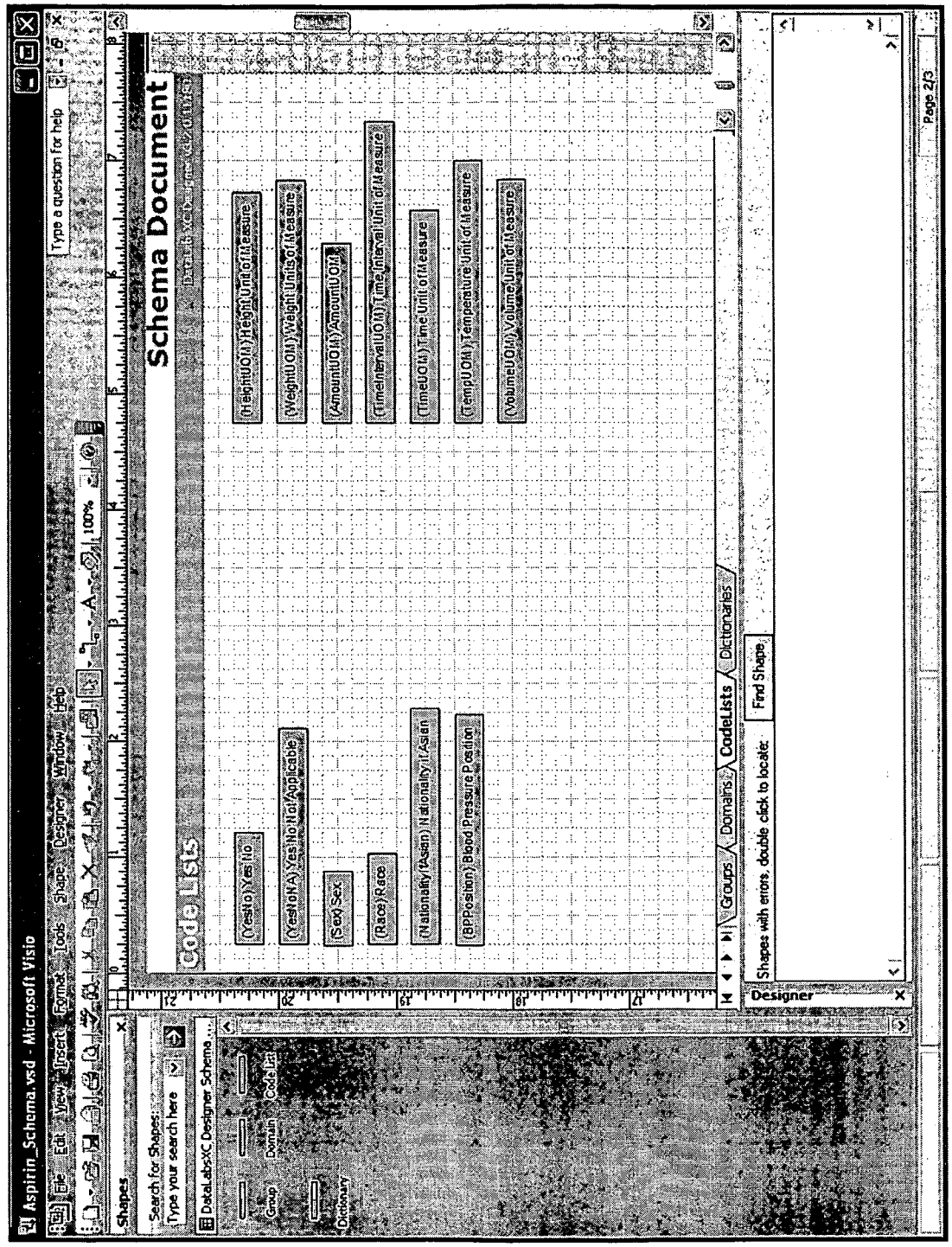
Figure 6K:
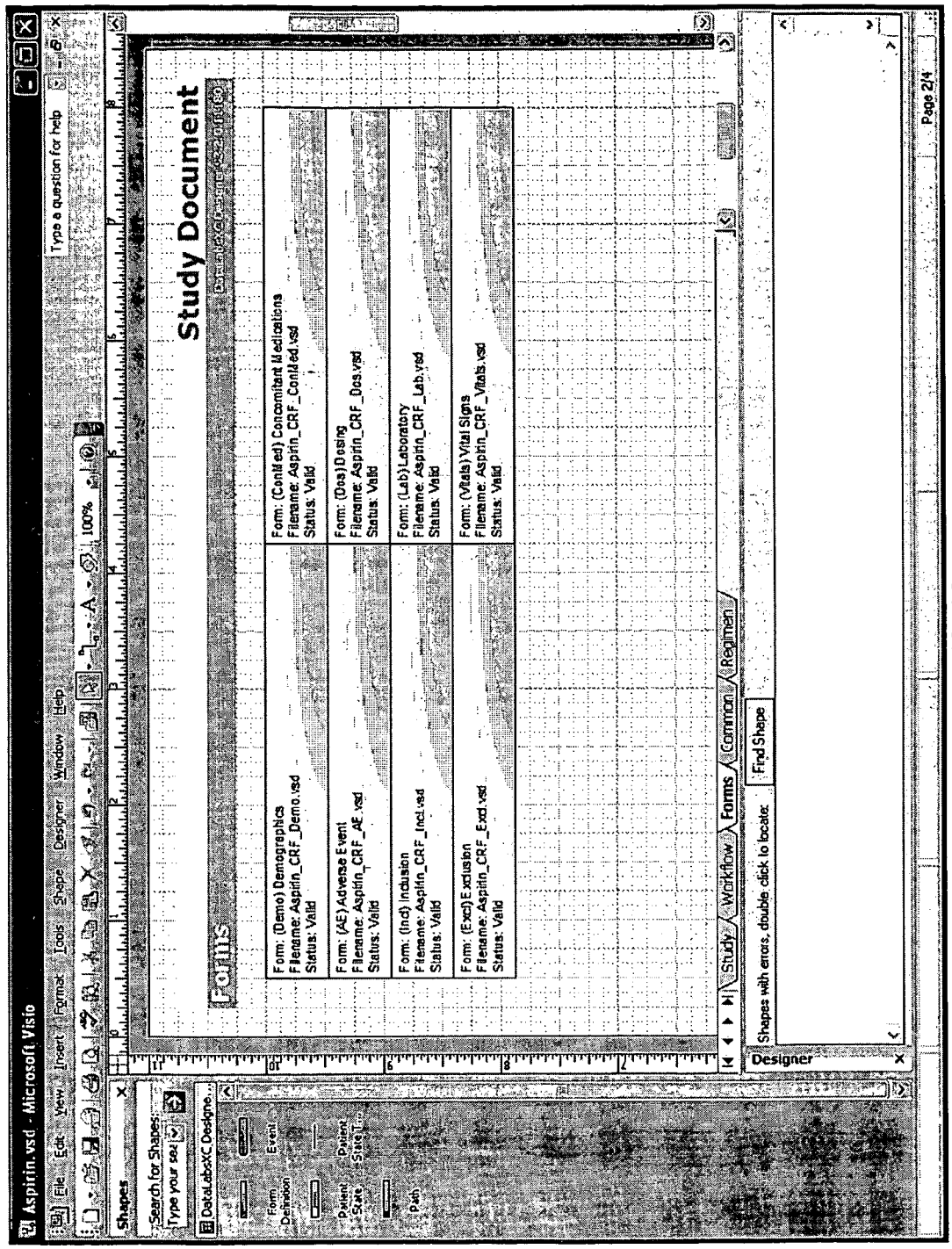
Figure 6L:
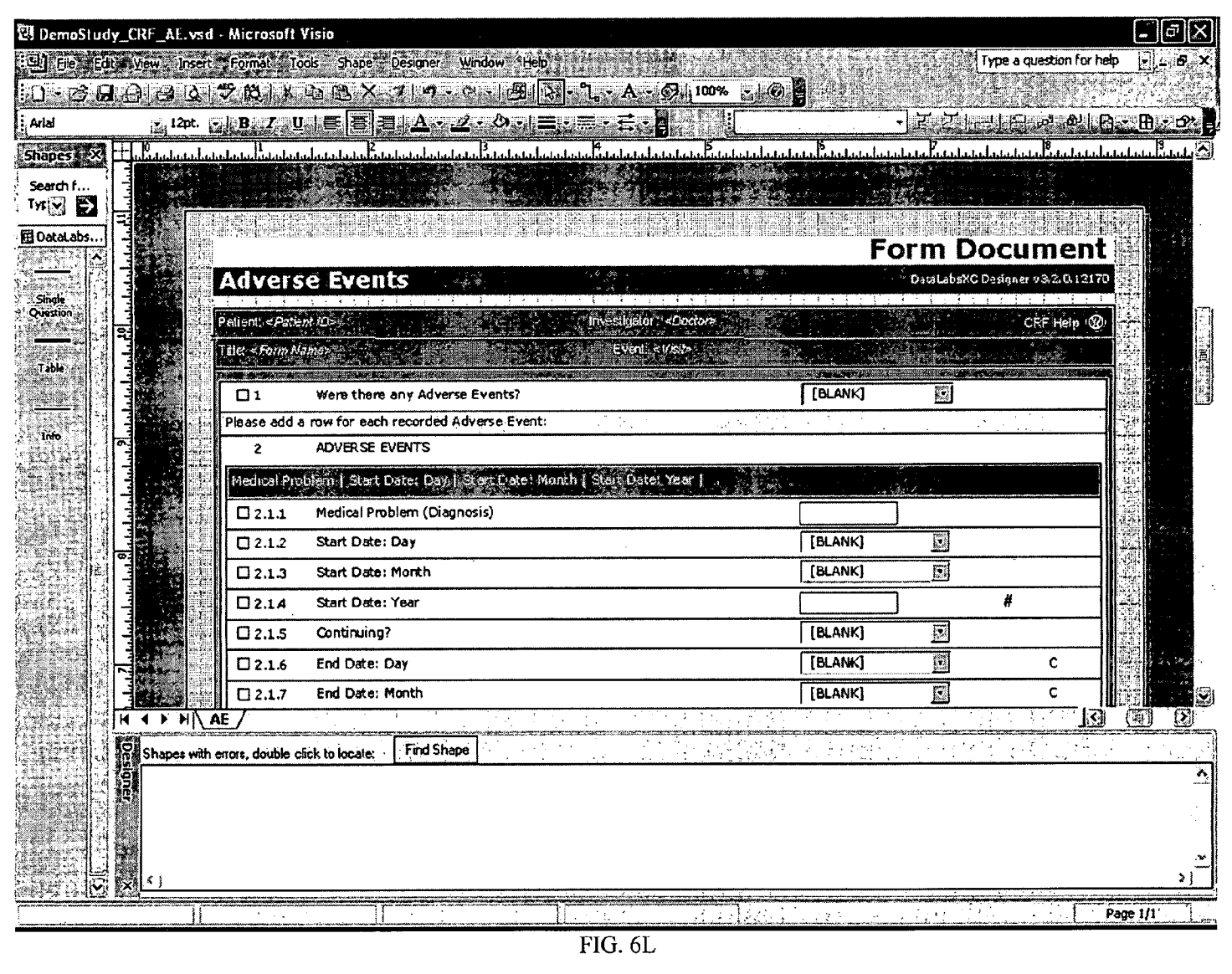
Figure 6M:
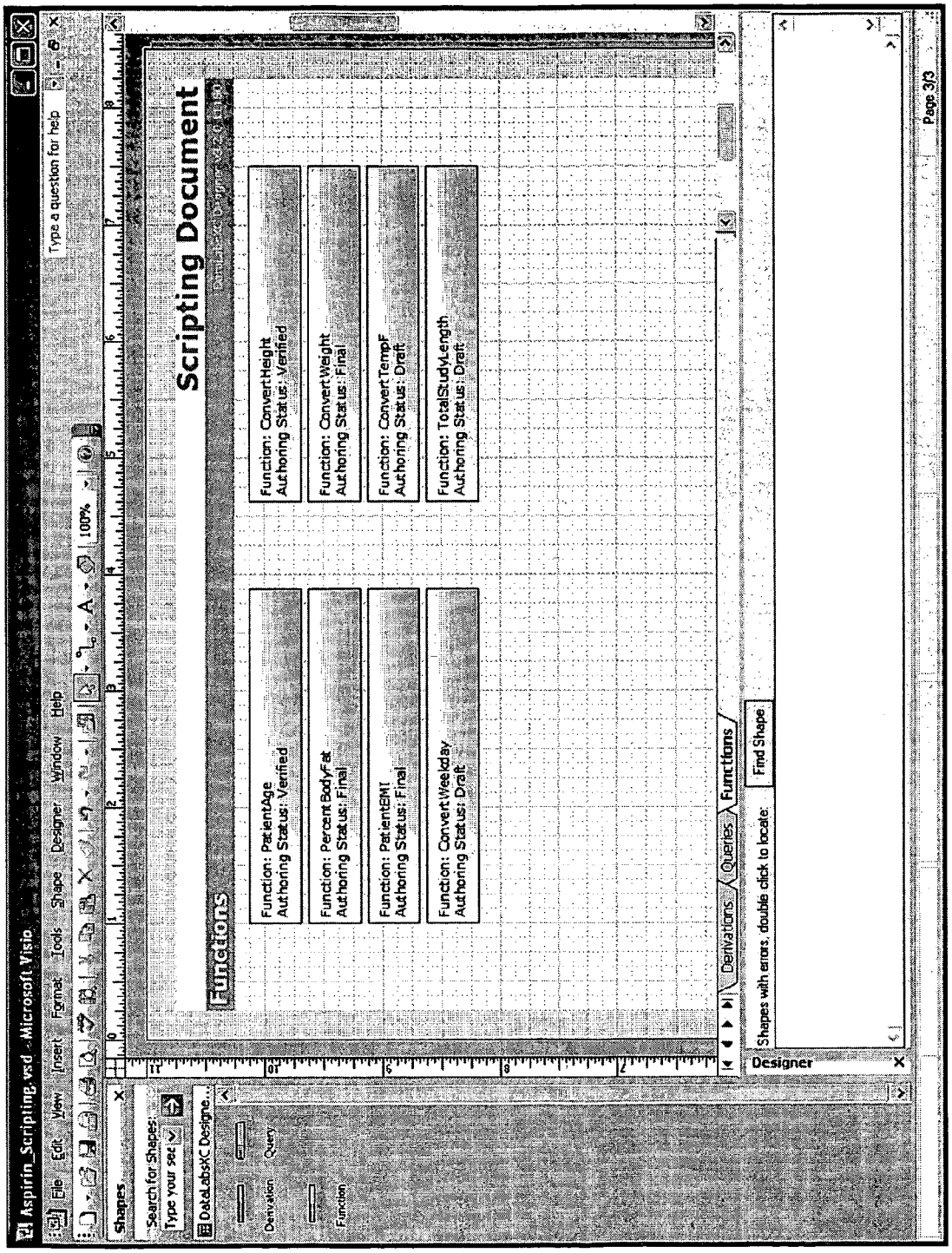
Figure 6N:
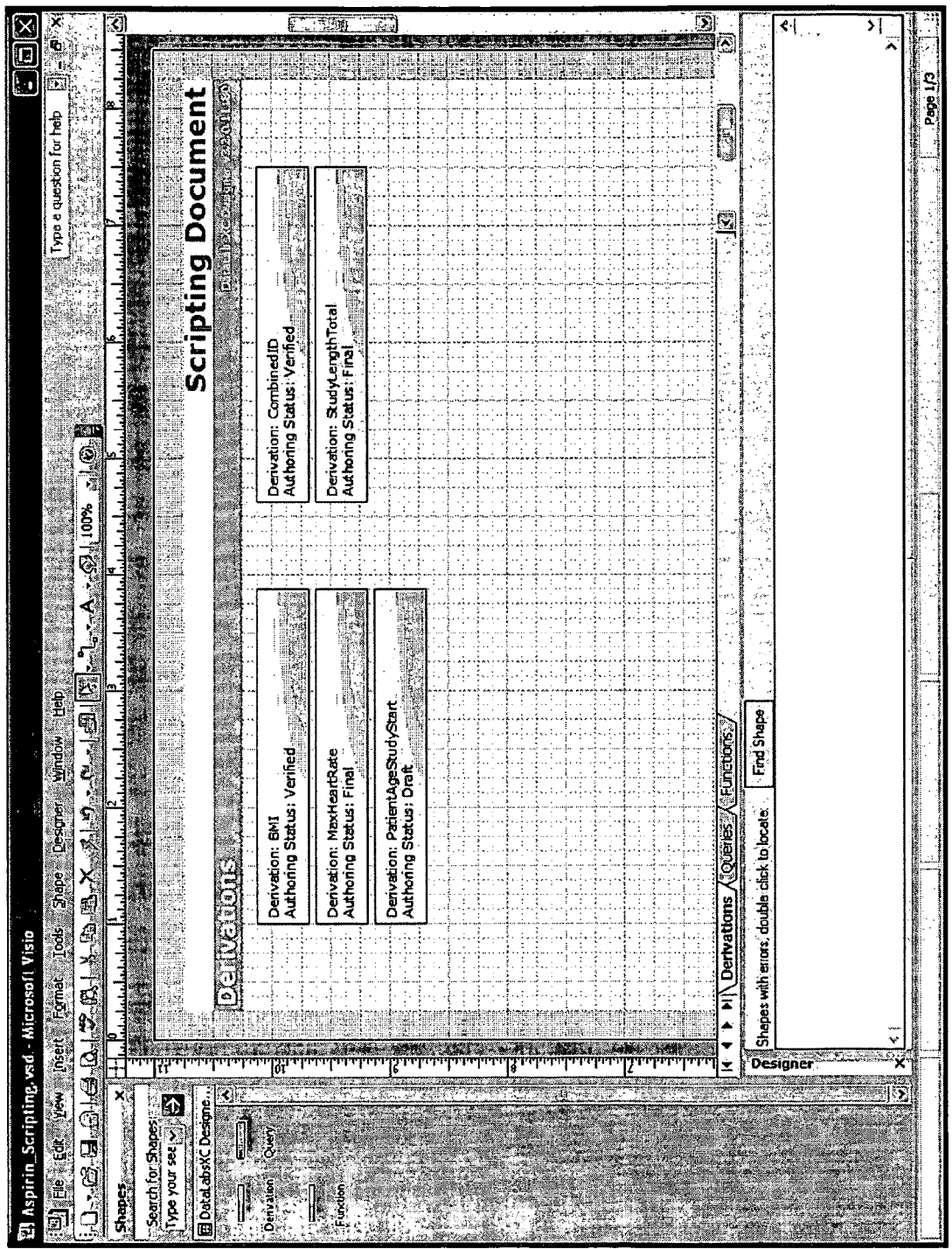
Figure 60:
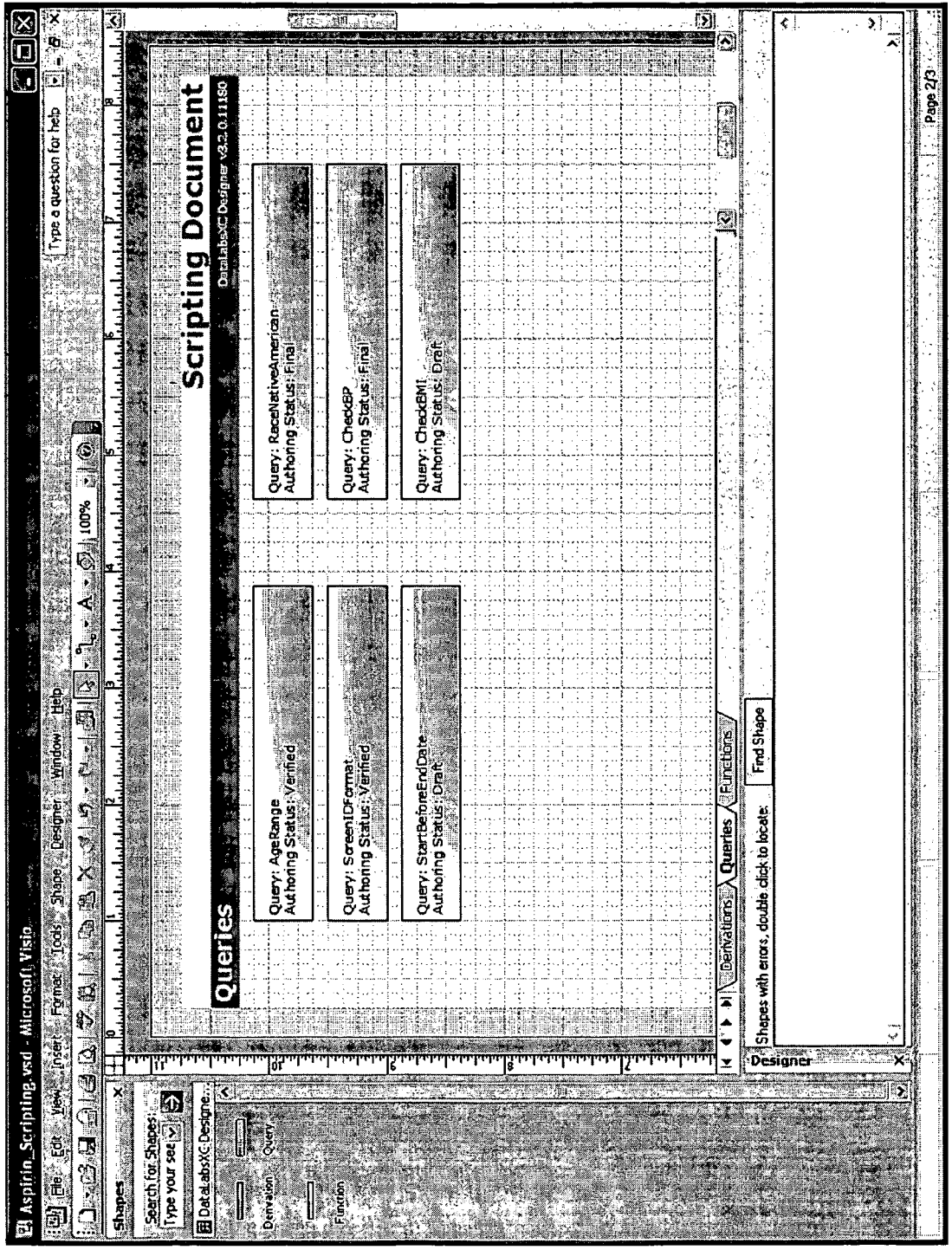
Figure 6P:
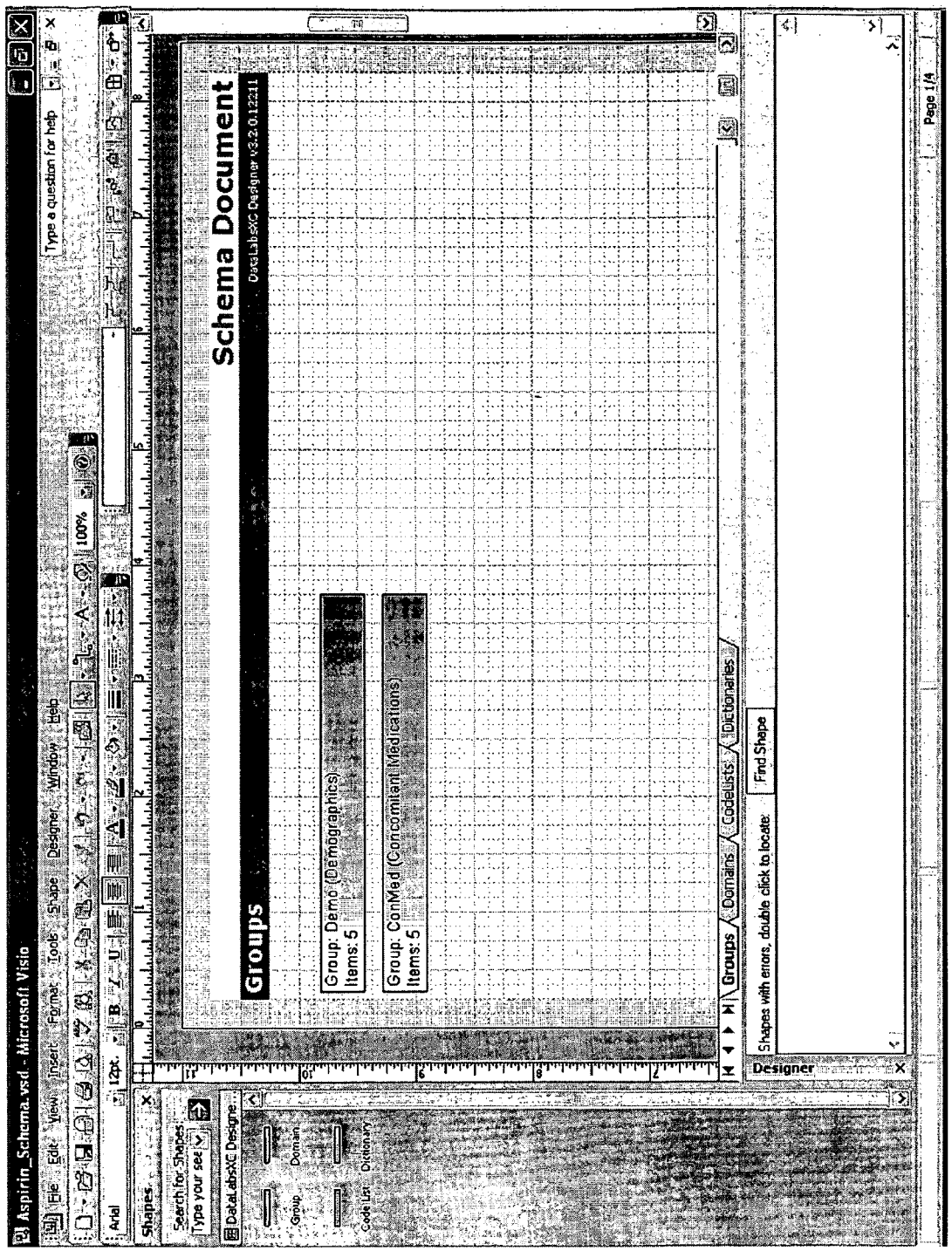

FIGS. 6A through 6P are exemplary simplified screen views illustrating embodiments of the designer program as it is applied in FIG. 5 for a simplified protocol for an Aspirin clinical trial. For example, FIG. 6A illustrates an exemplary screen view of Block 502, FIG. 6B illustrates an exemplary screen view of Block 503, FIG. 6C illustrates an exemplary screen view of Block 504, FIG. 6D illustrates an exemplary screen view of Block 506, FIG. 6E illustrates an exemplary screen view of Block 507, FIG. 6F illustrates an exemplary screen view of Block 508, FIG. 6G illustrates an exemplary screen view of Block 510, FIG. 6H illustrates an exemplary screen view of Block 514, FIG. 6I illustrates an exemplary screen view of Block 515, FIG. 6J illustrates an exemplary screen view of Block 512, FIG. 6K illustrates an exemplary screen view of Block 516, FIG. 6L illustrates an exemplary screen view of Block 518, FIG. 6M illustrates an exemplary screen view of Block 520, FIG. 6N illustrates an exemplary screen view of Block 522, FIG. 6O illustrates an exemplary screen view of Block 524, FIG. 6P illustrates an exemplary screen view of Block 526.

In particular, FIG. 6A illustrates an exemplary screen view of the Study Document 304 during the clinical trial design and Block 502. Stencils 602 are provided for each document that comprises the shapes that are associated with that particular document. With specific reference to the Study Document, shapes are dragged-and-dropped from a stencil onto the document in the conventional manner. That is, to drag a stencil the user clicks on the desired shape, and while holding down the left mouse button drags the shape onto the page and then releases the mouse button when the curser is in the desired position on the page. A skilled artisan will recognize from the disclosure herein a wide number of selection methodologies, including double or single click, or the like. Once dropped onto the document they appear as shapes 604. Tabs 606 are used to select various pages within the document. A page header 608 identifies the page as "Study", while a document identifier 610 identifies it as the "Study Document".

FIG. 6B illustrates an exemplary screen view of Block 503. From this screen, Patient State shapes can be added for each state that a Patient may obtain. They may be connected using Patient State Transition shapes to define a Workflow. For example, the Patient may start out as "Screened" and subsequently transition to be "Enrolled" or "Failed".

FIG. 6C illustrates an exemplary screen view of Block 504. From this screen, form shapes can be added for each Form that is collected during the course of a study. In this example, Demographics, Concomitant Medications, Adverse Event, Dosing, Inclusion, Laboratory, Exclusion and Vital Signs are Forms.

FIG. 6D illustrates an exemplary screen view of Block 506. The Common Event is a study event that is not associated with a particular time. According to one embodiment, the Common Event is used to collect forms that are universally available for collection e.g. Screening, Enrollment, and Adverse Events. In an embodiment, editing of the Common Event is optional.

FIG. 6E illustrates an exemplary screen view of Block 507. From this screen, Path shapes may be added to the Regimen Tab to define each sequence of Events that will be used in the study.

FIG. 6F illustrates an exemplary screen view of Block 508. In the described Aspirin study, an event can denote an interaction with a patient at which certain forms are collected. For this particular Aspirin study, FIG. 6F illustrates that there were four events added to the Path Document. The designer will assign some of the forms that have already been defined to each event.

FIG. 6G illustrates an exemplary screen view of Block 510. Dictionary shapes can be added for each encoding dictionary the study will use. According to one embodiment, the dictionary can be associated with a data item in a group. This defines a data item as encoded. For example, the dictionary may define that entries of "Bayer," "Bufferin," and "Anacin" will be translated into a standard "Aspirin" entry.

FIG. 6H illustrates an exemplary screen view of Block 514. Various kinds of domains can be created for the purpose of categorizing Groups and the Associated Data Items. For example, a demographics Domain shape can comprise data items for race, sex, age, etc. A vital signs Domain shape can comprise data items for blood pressure (systolic and diastolic), heart rate/pulse, respiration, etc. Additionally, a medical history Domain shape may comprise data items for medical conditions (past and present), family history, current treatment, etc. In this particular Aspirin Study, Demographics, Concomitant Medications, Laboratory Results, Vital Signs, Dosing, Inclusion, Exclusion, and Adverse Events are the Domains.

FIG. 6I illustrates an exemplary screen view of Block 515. Various kinds of groups can be created. Group shapes define a set of related data items.

FIG. 6J illustrates an exemplary screen view of Block 512. Code Lists are a list of (displayed and stored) values that will be used for the study.

FIG. 6K illustrates an exemplary screen view of Block 516. The designer may revert back to the Study Document 304, select the "Forms" tab and customize each of the individual Form documents associated with the foregoing Form shapes or add/remove additional shapes.

FIG. 6L illustrates an exemplary screen view of Block 518. This Adverse Event Form Document highlights that in an embodiment, each question represents one data item and questions outside of a table shape are collected once; while questions inside of a table shape are collected repeatedly in rows. Info shapes represent an informational section of the form. The designer can drag/drop shapes to change the order. Moreover, the designer can add Question shapes selecting the group and item, Table Question shapes that each may comprise one or more questions from one domain, and any Info shapes.

FIG. 6M illustrates an exemplary screen view of Block 520. Functions may include reusable logic that can be called by Derivation shapes and Query shapes. In an embodiment, designers may add any scripting function shapes that will be used by derivations or queries. The designer may advantageously select the parameters, author the functions, test the function results and the like.

FIG. 6N illustrates an exemplary screen view of Block 522. Derivations may include logic that calculates a value based on a set of entered or system parameters. Derivation shapes can be used to automatically populate a data item. The designer may advantageously add Derivation shapes, select functions, select parameters, author the derivation scripts, test the scripts, and the like.

FIG. 6O illustrates an exemplary screen view of Block 524. A designer may add Query shapes, select Parameters, select functions, author the query script, test the query results, and the like.

FIG. 6P illustrates an exemplary screen view of Block 526. Any unresolved or unassigned properties of data items in a Group shape can be remedied. Thereafter, the designing of the simplified Aspirin study is now complete and the designer can synchronize the clinical trial program to execute the Aspirin clinical trial.

Create New Study

FIGS. 7A through 7G combined form a flow chart illustrating another embodiment of a process for designing a clinical trial using the system of the present invention. To begin the study design process a new study is created by selecting Create New Study from the application menu. The Create New Study feature generates the stencils and documents for design of the study. As disclosed in the foregoing, each study may define one or more state transitions for a patient and may comprise one or more forms that are used to collect information about the patient participating in the clinical trial. Each form may be used one or more times as defined by the study design. Each unique form that is to be used in the study design is identified by opening the Study Document and dragging and dropping the Form shape from the stencil on to the document workspace. Properties are defined for each form by double clicking on the appropriate Form shape.

Each study may comprise one or more patient pathways (path). A path comprises a logical grouping of patient visits. Each unique path that is to be used in the study design is identified by opening the Study Document and dragging and dropping the Path shape from the stencil onto the document workspace. One path is identified as the primary path which is used as the default path for all new subjects.

Each study has a common event where forms can be displayed that are not associated with a particular patient visit. The Common shape is added to the Study document when the study is created. Forms associated with the common event are defined by double clicking on the Common shape and adding the forms from the list of forms already defined.

Each study has one or more patient visits. Unique visits are identified by opening the appropriate Path Document and dragging and dropping the Event shape from the stencil onto the document workspace. Properties are defined for each visit by double clicking on the appropriate Event shape. In addition, forms associated with the visit are added by selecting from the list of forms already defined.

Referring now to FIGS. 7A through 7G, a logical flow chart of the overall process of the present invention is shown. The process begins with a start button 700 (FIG. 7A) whereupon an inquiry 702 is made as to whether or not the user is creating a new study or opening an existing study. If the user is creating a new study, a new study 704 is created. At this step of the process, a new study document, a new scripting document, a new schema document and form documents for each default patient state are created. Also, a study shape is placed onto the study page of the study document, an event (common) shape is placed in the common page of the study document, and patient state shapes are placed on the workflow page of the study document. On the other hand if the user is opening an existing document, a default page 706 for the document is displayed. At this same step of the process, any pre-existing shapes on the page are displayed, and a stencil of the shapes that can be dragged onto the document are likewise displayed. This juncture of the process is referred to herein as TOP, which will be used as a reference point as explained herein below. Also, this begins the Study Document Forms Page. After this step, the process illustration is continued in FIG. 7B, as depicted by a connector A.

Referring now to FIG. 7B, and to the connector A in particular, the process next responds to a user dragging a form shape onto the forms page of the study document 708. An inquiry is made as to whether or not the process is to create from an existing form document 712. If the answer to this inquiry is no, then the user is solicited by the process to enter the form properties 710 and an empty new form document 714 is created. If the answer to this inquiry is yes, then the process solicits from the user what form document 716 to create the form from. Next, the existing form document is copied in order to create a new form document 718. At this juncture, the Study Document Regimen Page begins.

The process then responds to a user dragging a path shape onto the regimen page 720 of the study document. An inquiry is made as to whether or not the process is to create from an existing path document 724. If the answer is no, then the user is solicited by the process to enter the path properties 722 and an empty new path document 726 is created. After this step, the process illustration is continued in FIG. 7C, as depicted by a connector B1. If the answer to the inquiry is yes, then the process illustration continues in FIG. 7C as depicted by a connector B.

Figure 7C:
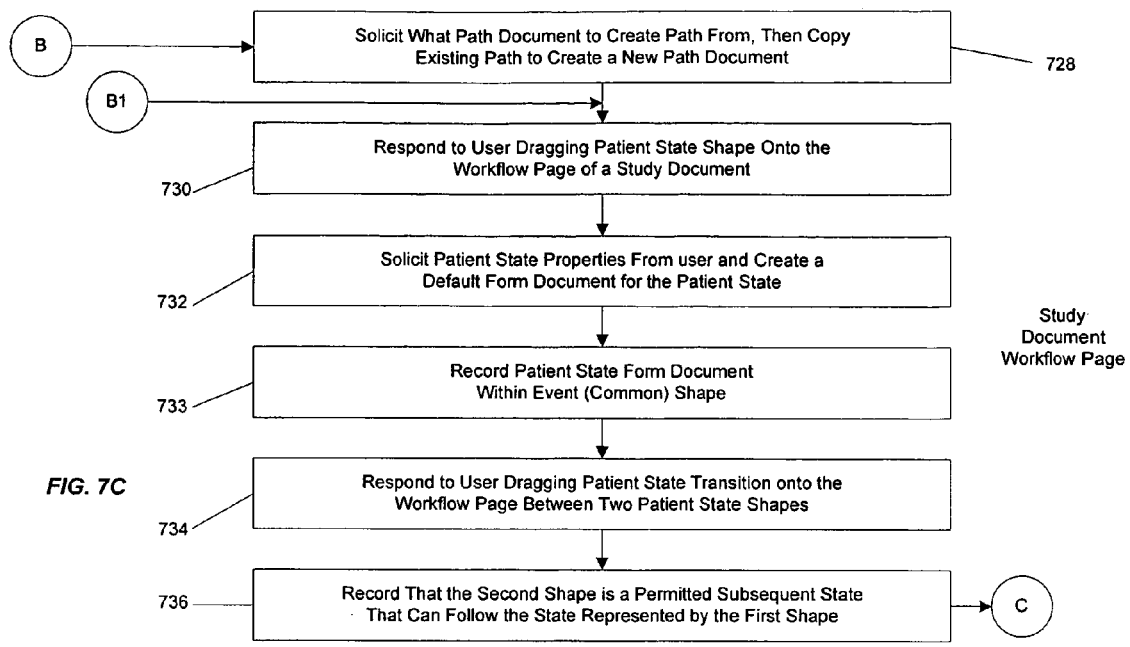

Referring now to FIG. 7C, and to the connector B in particular, the process now solicits from the user what path document to create from. The existing path is copied in order to create a new path document 728. After this, the Study Document Workflow Page begins. Next, and referring to the connector B1 in particular as well, the process responds to the user dragging a patient shape onto the workflow page of a study document 730. Then, the process solicits from the user the state properties and next creates a default form document for the patient state 732. The process then records the Patient State Form Document within an Event (Common) Shape 733. Following this, the process responds to the user dragging a patient transition shape state connector onto the workflow page between two patient state shapes 734. The fact that the second patient state is permitted, the subsequent state is recorded 736. The process illustration continues in FIG. 7D, as depicted by a connector C.

Figure 7D:
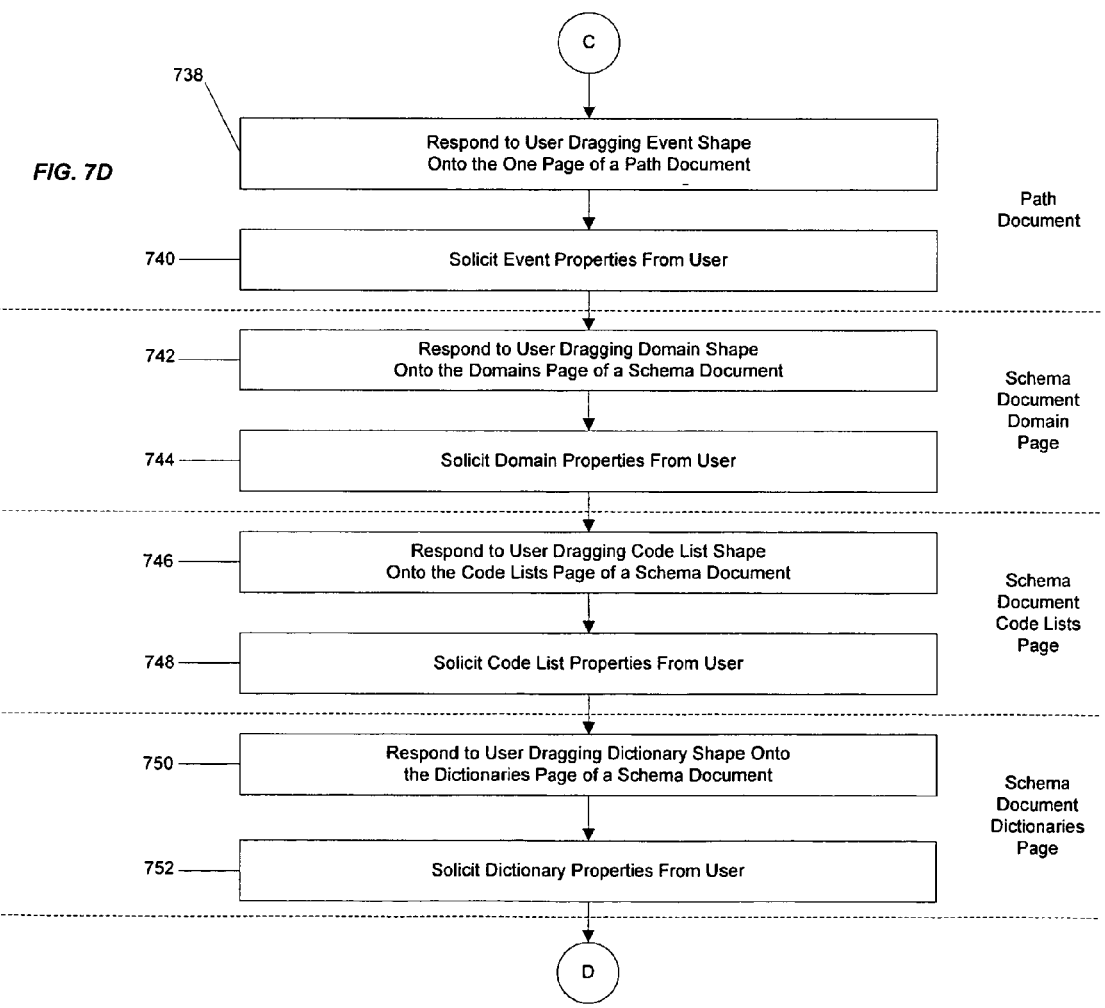

Referring now to FIG. 7D and to the connector C in particular, the process responds to the user dragging an event (visit) shape onto the one page of a path document 738. The process then solicits event (visit) properties 740 from the user and records the same. Next, the Schema Document Domain Page begins, whereupon the process responds to the user dragging a domain shape onto the domains page of a schema document 742. After this, the process solicits domain properties 744 from the user. At this juncture, the Schema Document Code Lists Page begins. The process then responds to the user dragging a code list shape onto the code lists page of a schema document 746, and then solicits from the user properties of the code list 748. The Schema Document Dictionaries Page next begins. The process again responds to the user dragging a dictionary shape onto the dictionaries page of a schema document 750. The process then solicits dictionary properties 752 from the user. The process illustration continues in FIG. 7E, as denoted by a connector D.

Figure 7E:
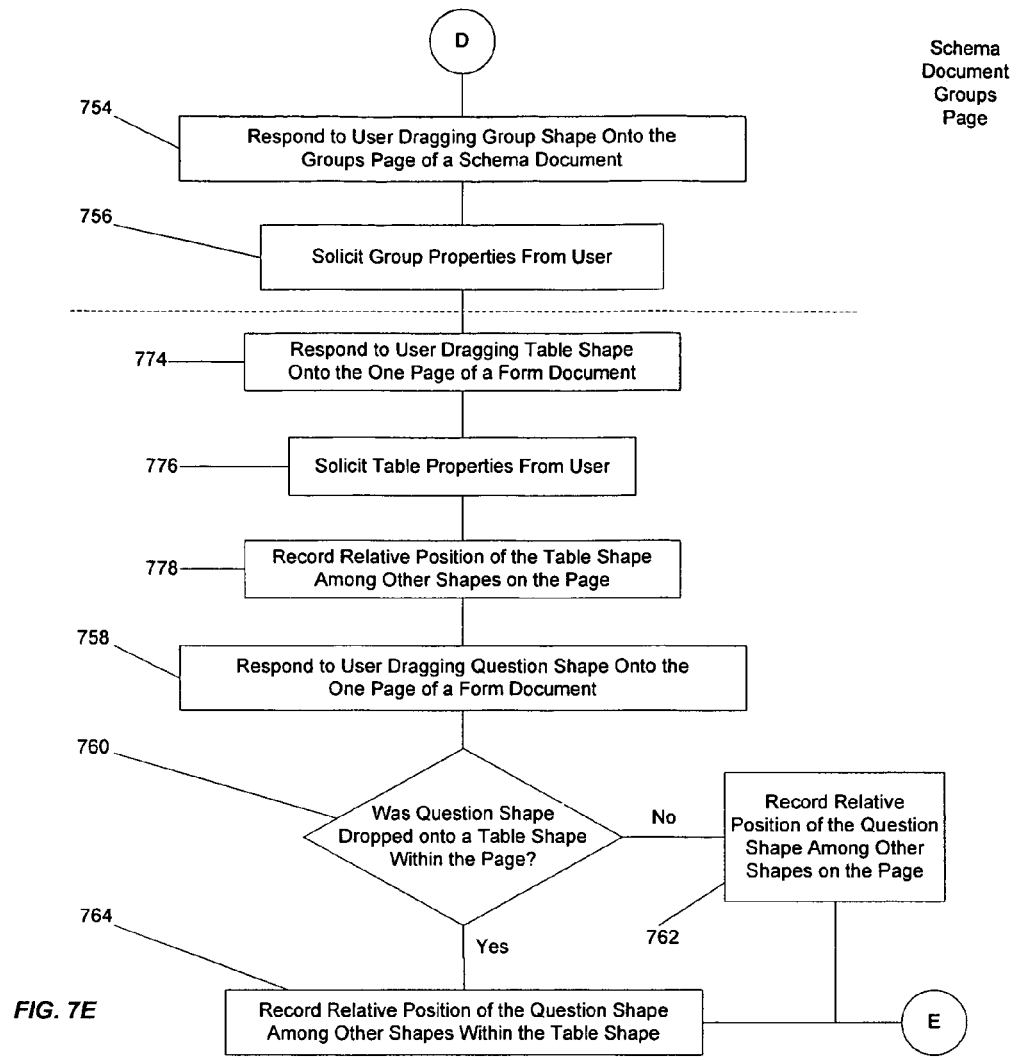

Referring now to FIG. 7E, and to the connector D in particular, the process responds to the user dragging a group shape onto the group page of a schema document 754. Next, the process solicits from the user group properties 756 and records the same. After this, the Form Document Form Page begins, wherein the process responds to the user dragging a table shape onto the one page of a form document 774, and then solicits table properties from the user 776. Following the above, the process records the relative position of the table shape among other shapes on the page 778. After this, the process then responds to a user dragging a question shape onto the one page of a form document 758. An inquiry is next made as to whether or not the question shape was dropped onto a table shape within the page 760. If the answer to this inquiry is no, then the relative position of the question shape among the other shapes on the page is recorded 762. Following this, or if the answer to the inquiry is yes, the relative position of the question shape among other shapes within the table shape is recorded 764. The process illustration continues in FIG. 7F as depicted by a connector E.

Figure 7F:
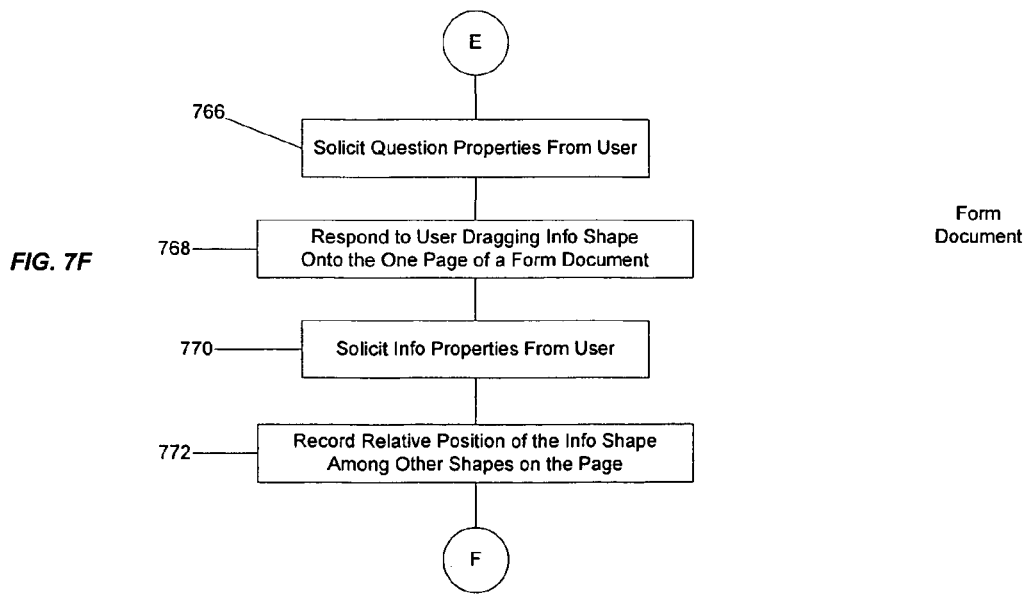

Referring now to FIG. 7F, and to the connector E in particular, the process solicits from the user properties for the question 766. Next, the process responds to a user dragging an info shape onto the one page of a form document 768, and then solicits info properties from the user 770. After this, the process records the relative position of the info shape among other shapes on the page 772. The process illustration continues in FIG. 7G as depicted by a connector F.

Figure 7G:
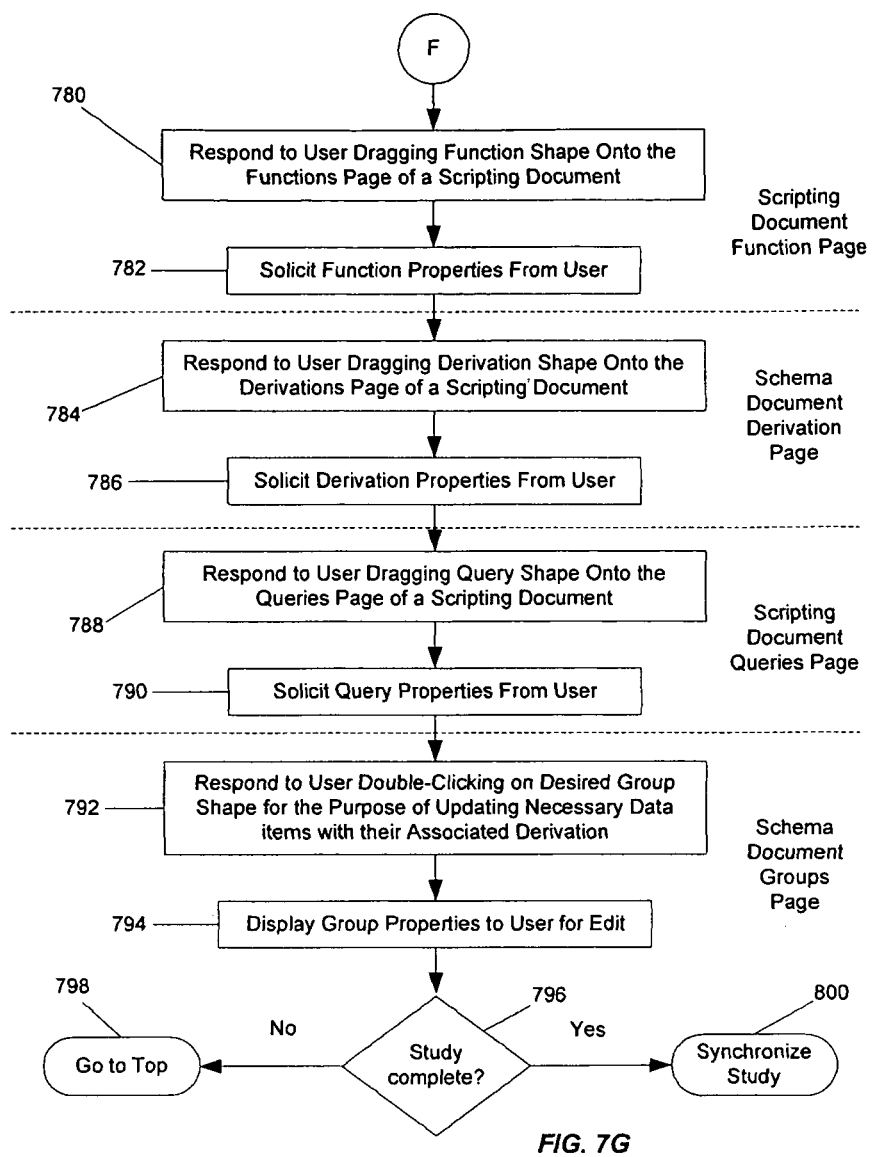

Referring now to FIG. 7G, and to the connector F in particular, the Scripting Document Function Page begins, whereupon the process responds to the user dragging a function shape onto the functions page of a scripting document 780. Next, the process solicits the function properties from the user 782. After this, the Schema Document Derivation Page begins, wherein the process responds to the user dragging a derivation shape onto the derivations page of a scripting document 784, and then solicits derivation properties from the user 786. At this juncture, the Scripting Document Queries Page begins, whereupon the process responds to the user dragging a query shape onto the queries page of a scripting document 788, and then solicits from the user the query properties 790. The process then returns to the Schema Document Groups Page, whereupon the process responds to the user double-clicking on the desired group shape for the purpose of updating necessary data items with the Associated Derivations 792. The process then displays the Group Properties to User for Edit. At this juncture, the process inquires as to whether or not the user has completed the study and does not need to make any edits 796. If the answer to this inquiry is no, then the process returns back to the TOP 798. On the other hand, if the user has completed the study, the process ends and the Study will be Synchronized 800.

Although the invention has been described with reference to a specific embodiment, this description is not meant to be construed in a limiting sense. Various modifications of the disclosed embodiment as well as alternative embodiments of the invention will become apparent to one skilled in the art upon reference to the description of the invention. It is therefore contemplated that the appended claims will cover any such modifications of embodiments that fall within the true scope of the invention.

Although the foregoing invention has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A designer program capable of providing tools for configuring a clinical trial program to execute a protocol of a clinical trial, the clinical trial program comprising a data capture and data management system capable of collecting data from geographically disparate users, the designer program comprising computer executable instructions encoded on a non-transitory computer readable medium that, when executed on at least one computer system perform a method comprising:

receiving, through a user interface, user input representing a plurality of components of a clinical trial, the plurality of components comprising:
at least one event representing a patient visit;
at least one path representing a sequence of patient visits;
a plurality of data items;
at least one form; and
at least one domain, each domain defining a relationship between at least some of the plurality of data items wherein the relationship defined in each domain reflects a logical grouping of the at least some of the data items for reporting and/or exporting the at least some of the data items, wherein the logical grouping is distinct from the protocol of the clinical trial,
wherein the user interface comprises:
a stencil window comprising a plurality of shapes, each shape representing at least one of the plurality of components of the clinical trial and each shape including customizable properties, the plurality of shapes including a Domain shape representing the at least one domain; and one or more design windows capable of accepting ones of the plurality of shapes selected by a designer from the stencil window, wherein selection of the ones of the plurality of shapes and subsequent editing of their customizable properties allow a designer to model a protocol of a clinical trial;

dynamically generating or modifying, based on the user input, at least one configuration file for the clinical trial program, wherein the at least one configuration file includes one or more instructions for configuring the clinical trial program to execute the protocol of the clinical trial; and generating a report or data export, wherein the report or data export is generated based, at least in part, on the at least one domain as specified in the at least one configuration file.

2. The designer program of claim 1, further comprising an output command capable of generating the at least one configuration file, wherein the clinical trial program comprises a data capture and data management system capable of collecting data from geographically disparate users.

3. The designer program of claim 1, wherein the plurality of components include validation scripts.

4. The designer program of claim 3, wherein the designer program is capable of performing positive or negative testing on the validation scripts.

5. The designer program of claim 1, wherein the plurality of shapes include at least one of a drag-and-drop action, a double-click action, or a single click action.

6. The designer program of claim 1, wherein the at least one configuration file comprises one or more XML documents.

7. The designer program of claim 1, wherein the plurality of shapes include a Form shape and an Event shape.

8. The designer program of claim 1, wherein the plurality of shapes include two or more of the following shapes: a Study shape, a Form shape, an Event shape, a Common Event shape, a Patient State shape, a Patient State Transition shape, a Path shape, a Domain shape, a CodeList shape, a Dictionary shape, a Question shape, a Table shape, an Information shape, a Derivation shape, a Query shape, and a Function shape.

9. The designer program of claim 1, wherein content of the design windows are stored as documents.

10. The designer program of claim 9, wherein one or more of the documents maintains relationships with others of the documents.

11. The designer program of claim 9, wherein the documents comprise at least two of the following documents:
a. a study document for maintaining said relationships, said study document being disposed for defining study properties, form definitions, common forms, study regimen (such as paths) and patient workflow;
b. one or more form documents being disposed for defining presentations for user interaction, including text and fields for collecting data as part of said clinical trial;
c. one or more path documents being disposed for defining a sequence of patient visits for a particular path including those forms that are to be collected at each patient visit;
d. a scripting document being disposed for defining complex logic that is run against data entered as part of said clinical trial; and,
e. a schema document being disposed for defining data items that can be referenced within a form.

12. The designer program of claim 11 wherein said study document includes at least one of:
a. a study shape;
b. one or more patient state transition shapes;
c. one or more path shapes;
d. one common event shape; and
e. one or more form shapes.

13. The designer program of claim 11 wherein said form documents include at least one of:
a. one or more info shapes;
b. table shapes; and
c. question shapes.

14. The designer program of claim 11 wherein said path documents includes one or more event shapes.

15. The designer program of claim 11 wherein said scripting documents include at least one of:
a. one or more derivation shapes;
b. one or more query shapes; and
c. one or more function shapes.

16. The designer program of claim 11 wherein said schema document includes at least one of:
a. one or more domain shapes;
b. one or more group shapes;
c. one or more code list shapes; and
d. one or more dictionary shapes.

17. A method of configuring a clinical trial program to execute a clinical trial protocol, the clinical trial program comprising a data capture and data management system capable of collecting data from geographically disparate users, the method comprising:
with at least one computer system:
receiving, via a user interface, user input comprising configuration instructions for the clinical trial program to configure the clinical trial program to a particular protocol by specifying a plurality of components of the clinical trial, the plurality of components comprising:
at least one event representing a patient visit;
at least one path representing a sequence of patient visits;
at least one form defining information presented a user via the clinical trial program associated with the at least one event;
a plurality of data items collected through the at least one form; and
at least one domain, each domain defining a relationship between at least some of the plurality of data items to facilitate reporting and/or data exporting of the at least some of the plurality of data items by enabling at least one user of the clinical trial program to generate reports and/or outputs based on the relationship defined in the domain;
wherein the user interface comprises:
a stencil window comprising a plurality of shapes, each shape representing at least one of the plurality of components of the clinical trial and each shape including customizable properties, the plurality of shapes including a Domain shape representing the at least one domain; and
one or more design windows capable of accepting ones of the plurality of shapes selected by a designer from the stencil window, wherein selection of the ones of the plurality of shapes and subsequent editing of their customizable properties allow a designer to model a protocol of a clinical trial;

generating or modifying, based on the configuration instructions, one or more instructions for configuring the clinical trial program to execute the protocol of the clinical trial, wherein the one or more instructions include instructions for configuring a database system for storing data of the clinical trial; and generating a report or data export, wherein the report or data export is generated based, at least in part, on the at least one domain.

18. The method of claim 17, wherein:
receiving user input comprises receiving a selection of ones of the plurality of shapes representing the plurality of components; and wherein the method further comprises customizing the customizable properties of one or more of the selected ones of the plurality of shapes representing the plurality of components to model the protocol of the clinical trial,
wherein the customizing comprises executing validation scripts.

19. The designer program of claim 1, further comprising computer executable instructions that organize a set of data items into logical categories for data export based on a respective domain that defines the logical categories.

20. The designer program of claim 1, wherein the one or more instructions include instructions for configuring a database system for storing data of the clinical trial.

21. The method of claim 17, wherein:
receiving user input comprises receiving a selection of ones of the plurality of shapes; and
wherein the plurality of shapes include at least one of a drag-and-drop action, a double-click action, or a single click action.

22. The method of claim 21, wherein the plurality of shapes include a Form shape, an Event shape, and a Group shape.

23. The method of claim 21, wherein the plurality of shapes include at least the following shapes: a Study shape, a Form shape, an Event shape, a Common Event shape, a Patient State shape, a Patient State Transition shape, a Path shape, a Domain shape, a Group shape, a CodeList shape, a Dictionary shape, a Question shape, a Table shape, an Information shape, a Derivation shape, a Query shape, and a Function shape.

24. The method of claim 17, wherein each domain defines logical categories that organize a respective set of data items for data export.

* * * * *